US 008781854B1

(12) United States Patent
Harris, Sr.

(10) Patent No.: US 8,781,854 B1
(45) Date of Patent: Jul. 15, 2014

(54) SYSTEMS AND METHODS FOR IDENTIFYING HEALTHCARE TRANSACTIONS WITH A RISK OF FAILING TO INCLUDE APPROPRIATE DIRECTIONS FOR USE

(75) Inventor: Patrick Harris, Sr., Atlanta, GA (US)

(73) Assignee: McKesson Financial Holdings (BM)

( * ) Notice: Subject to any disclaimer, the term of this patent is extended or adjusted under 35 U.S.C. 154(b) by 309 days.

(21) Appl. No.: 13/208,811

(22) Filed: Aug. 12, 2011

(51) Int. Cl.
*G06Q 10/00* (2012.01)
*G06Q 50/22* (2012.01)

(52) U.S. Cl.
CPC .................. *G06Q 50/22* (2013.01)
USPC ........................................... 705/2

(58) Field of Classification Search
CPC ....... G06Q 50/22; G06Q 50/24; G06Q 40/08; G06Q 705/02; G06Q 705/03; G06Q 600/30; G06Q 705/04; G06F 19/322; G06F 19/3456
USPC ...................... 705/2, 3, 4; 600/300
See application file for complete search history.

(56) References Cited

U.S. PATENT DOCUMENTS

| | | | |
|---|---|---|---|
| 5,628,530 A | 5/1997 | Thornton | |
| 6,012,035 A | 1/2000 | Freeman et al. | |
| 6,195,612 B1 | 2/2001 | Pack-Harris | |
| 6,757,898 B1 | 6/2004 | Ilsen et al. | |
| 6,769,228 B1 | 8/2004 | Mahar | |
| 7,155,397 B2 | 12/2006 | Alexander et al. | |
| 7,401,027 B2 | 7/2008 | Moore et al. | |
| 7,761,311 B2 * | 7/2010 | Clements et al. | 705/3 |
| 7,797,172 B2 | 9/2010 | Fitzgerald et al. | |
| 8,244,556 B1 | 8/2012 | Ringold | |
| 8,489,411 B1 | 7/2013 | Rowe et al. | |
| 8,682,697 B1 | 3/2014 | Harris | |
| 2001/0037216 A1 | 11/2001 | Oscar et al. | |
| 2002/0002495 A1 | 1/2002 | Ullman | |
| 2002/0087583 A1 | 7/2002 | Morgan et al. | |

(Continued)

FOREIGN PATENT DOCUMENTS

| | | |
|---|---|---|
| CA | 2482370 A1 | 3/2006 |
| WO | WO 9503569 A3 | 2/1995 |
| WO | WO 0039737 A1 | 7/2000 |
| WO | WO 2007025295 A2 | 3/2007 |

OTHER PUBLICATIONS

Non-final Office Action for U.S. Appl. No. 12/731,269 mailed Jan. 13, 2012.

(Continued)

*Primary Examiner* — Michelle L Le
(74) *Attorney, Agent, or Firm* — Sutherland Asbill & Brennan LLP

(57) ABSTRACT

Systems and methods for identifying healthcare transactions with a risk of failing to include appropriate directions for use are provided. A healthcare claim transaction may be received from a healthcare provider computer. Based upon an analysis of the received healthcare claim transaction, identification information for a prescriber may be determined. A determination may be made as to whether the identified prescriber is an at-risk prescriber that has previously failed to include appropriate directions for use in association with a prescription. If it is determined that the prescriber is an at-risk prescriber, then a predetermined control action may be implemented. Otherwise, if it is determined that the prescriber is not an at-risk prescriber, then the healthcare claim transaction may be communicated to a claims processor computer associated with a claims processor.

18 Claims, 7 Drawing Sheets

(56) References Cited

U.S. PATENT DOCUMENTS

| | | |
|---|---|---|
| 2002/0111832 A1 | 8/2002 | Judge |
| 2002/0188476 A1* | 12/2002 | Bienvenu et al. .................. 705/3 |
| 2002/0198831 A1 | 12/2002 | Patricelli et al. |
| 2003/0009367 A1 | 1/2003 | Morrison |
| 2003/0050799 A1 | 3/2003 | Jay et al. |
| 2003/0069760 A1 | 4/2003 | Gelber |
| 2003/0083903 A1 | 5/2003 | Myers |
| 2003/0149625 A1 | 8/2003 | Leonardi et al. |
| 2003/0154163 A1 | 8/2003 | Phillips et al. |
| 2003/0229540 A1 | 12/2003 | Algiene |
| 2004/0006490 A1 | 1/2004 | Gingrich et al. |
| 2004/0039599 A1 | 2/2004 | Fralic |
| 2004/0054685 A1 | 3/2004 | Rahn |
| 2004/0073457 A1 | 4/2004 | Kalies |
| 2004/0078234 A1 | 4/2004 | Tallal, Jr. et al. |
| 2004/0117323 A1 | 6/2004 | Mindala |
| 2004/0148198 A1 | 7/2004 | Kalies |
| 2004/0249745 A1 | 12/2004 | Baaren |
| 2005/0015280 A1 | 1/2005 | Gabel et al. |
| 2005/0060201 A1 | 3/2005 | Connely, III et al. |
| 2005/0102169 A1 | 5/2005 | Wilson |
| 2005/0137912 A1 | 6/2005 | Rao et al. |
| 2005/0154627 A1 | 7/2005 | Zuzek et al. |
| 2005/0187793 A1 | 8/2005 | Myles |
| 2005/0197862 A1 | 9/2005 | Paterson et al. |
| 2005/0240473 A1 | 10/2005 | Ayers, Jr. et al. |
| 2005/0288972 A1 | 12/2005 | Marvin et al. |
| 2006/0020514 A1 | 1/2006 | Yered |
| 2006/0026041 A1 | 2/2006 | Ullman |
| 2006/0085230 A1 | 4/2006 | Brill et al. |
| 2006/0149784 A1 | 7/2006 | Tholl et al. |
| 2006/0184391 A1 | 8/2006 | Barre et al. |
| 2006/0212318 A1 | 9/2006 | Dooley |
| 2006/0217824 A1* | 9/2006 | Allmon et al. .................. 700/90 |
| 2006/0259363 A1 | 11/2006 | Jhetam et al. |
| 2007/0005402 A1 | 1/2007 | Kennedy et al. |
| 2007/0050209 A1 | 3/2007 | Yered |
| 2007/0136100 A1 | 6/2007 | Daugherty et al. |
| 2007/0233525 A1 | 10/2007 | Boyle |
| 2007/0233526 A1 | 10/2007 | Hoffman et al. |
| 2007/0239493 A1 | 10/2007 | Sweetland et al. |
| 2008/0097903 A1* | 4/2008 | Boyle ............................ 705/40 |

OTHER PUBLICATIONS

Sampson, R.J., Taking Control of Health Care Costs, Best's Review—Life Health Insurance Edition, Nov. 1983, pp. 64-66, vol. 84, Issue 7, USA.

Anonymous, ACS to Demonstrate Electronic Health Record Solution Suite at MMIS 2007 Conference; EHR Tools Consolidate Data, Provide Useful Information at the Point of Care for Medicaid Providers, Payers, and Patients, PR Newswire, Aug. 13, 2007, New York, NY, USA.

Lamb, J., New Era of Electronic Medicine Management: E-Prescriptions, Britain's Traditionally Cautious National Health Service is Starting Trials for Online Prescription, with the Aim of Cutting Costs. Financial Times, London, Feb. 21, 2001, p. 6, London, United Kingdom.

Anonymous, Pharmacy Industry Leaders Launch Firm to Supply Real-Time Data. PR Newswire. Jul. 30, 2001, p. 1, New York, NY, USA.

Anonymous, Medic; On-line Goes In-House, Chain Store Age Executive, Jan. 1987, pp. 128-132. vol. 63, Issue 1, USA.

Anonymous, TechRx Announces Successful Beta Deployment of T-Rex. PR Newswire. May 13, 2002.

Navitus, "Pharmacy Adjudication Alternative to WAP" Pharmacy Benefits Academy Aug. 19, 2010.

ViewPoints, "AWP Litigation Means Rapid Change Ahead" Nov./Dec. 2008.

State of Mississippi, Division of Medicaid, Provider Policy Manual May 1, 2008.

Paduda, Joseph, "Managed Care Matters" from comments, 2006.

Pennsylvania Department of Aging, "Acquisition Cost-Based Pricing for the PACE Program" Feb. 20, 2009.

Non-Final Office Action for U.S. Appl. No. 11/759,767 mailed Jul. 9, 2009.

Final Office Action for U.S. Appl. No. 11/759,767 mailed Dec. 24, 2009.

Non-final Office Action for U.S. Appl. No. 12/415,134, mailed Apr. 6, 2011.

Non-final Office Action for U.S. Appl. No. 12/327,100 mailed May 11, 2011.

Non-final Office Action for U.S. Appl. No. 11/759,767 mailed Jun. 24, 2011.

Final Office Action for U.S. Appl. No. 12/731,269 mailed Mar. 15, 2013.

Notice of Allowance for U.S. Appl. No. 11/759,767 mailed Apr. 25, 2013.

Laury, Susan K.; McInnes, Melayne Morgan; "The impace of insurance prices on decision making biases: An experimental analysis;" Jun. 2003; Journal of Risk & Insurance; vol. 70 No. 2; ISSN: 0022-4367.

Irvine, Benedict; "Health care superieur: Does the UK need French lessons;" May/Jun. 2001; Consumer Policy Review, vol. 11 No. 3; pp: 92-100; Journal Code: CPW.

Knight-Ridder Tribune Business News; "Milwaukee-Area Businesses Initiate Plan to Cut Health Costs;" Sep. 2, 2003; Supplier No. 107223132.

Non-Final Office Action for U.S. Appl. No. 12/731,269 mailed Jun. 25, 2013.

Non-final Office Action for U.S. Appl. No. 12/731,269 mailed Oct. 19, 2012.

Final Office Action for U.S. Appl. No. 12/731,269 mailed Jun. 19, 2012.

Final Office Action for U.S. Appl. No. 12/327,100 mailed Oct. 17, 2011.

Final Office Action for U.S. Appl. No. 11/759,767 mailed Dec. 6, 2011.

* cited by examiner

SYSTEMS AND METHODS FOR IDENTIFYING HEALTHCARE TRANSACTIONS WITH A RISK OF FAILING TO INCLUDE APPROPRIATE DIRECTIONS FOR USE

FIELD OF THE INVENTION

Aspects of the invention relate generally to healthcare transactions, and more particularly, to identifying healthcare transactions having a risk of failing to include appropriate directions for use.

BACKGROUND OF THE INVENTION

Healthcare providers, such as pharmacies, typically generate healthcare claim transactions on behalf of patients or customers. Once generated, the healthcare claim transactions are typically output for communication to payers and claims processors for adjudication purposes. Healthcare transactions are then typically completed following the adjudication of the relevant claim transactions. For example, drugs and/or other products are typically dispensed to patients or customers.

Following the completion of a healthcare transaction, there is a possibility that the healthcare claim transaction and/or the underlying healthcare transaction will be audited. For example, a claims adjudicator or payer may conduct or direct the completion of an audit relating to a healthcare transaction. Any discrepancy found with the healthcare transaction during an audit often leads to a charge-back, thereby resulting in a financial loss for the healthcare provider. Audit activity has steadily increased in recent years. One of the top economic audit issues impacting healthcare providers relates to "directions for use" information associated with prescriptions. In the event that a physician fails to provide appropriate and/or specific directions for use that satisfy payer or adjudicator guidelines, a charge-back is typically generated.

The problem with insufficient directions for use information is compounded because directions for use information is not included in healthcare claim transactions. The current National Council for Prescription Drug Programs ("NCPDP") telecommunications standard does not support the inclusion of directions for use information. Accordingly, healthcare claim transactions cannot currently be evaluated in order to determine whether appropriate directions for use have been provided for a product by a prescribing physician. Therefore, an opportunity exists for improved systems and methods for identifying healthcare transactions with a risk of failing to include appropriate directions for use.

BRIEF DESCRIPTION OF THE INVENTION

Some or all of the above needs and/or problems may be addressed by certain embodiments of the invention. Embodiments of the invention may include systems and methods for identifying healthcare transactions with a risk of failing to include appropriate directions for use. In one embodiment, a computer-implemented method may be provided. A healthcare claim transaction may be received from a healthcare provider computer associated with a healthcare provider. Based upon an analysis of the received healthcare claim transaction, identification information for a prescriber associated with the healthcare claim transaction may be determined. A determination may be made as to whether the identified prescriber is an at-risk prescriber that has previously failed to include appropriate directions for use in association with a prescription. If it is determined that the prescriber is an at-risk prescriber, then a predetermined control action may be implemented. Otherwise, if it is determined that the prescriber is not an at-risk prescriber, then the healthcare claim transaction may be communicated to a claims processor computer associated with a claims processor. In certain embodiments, the above operations may be performed by one or more computers associated with a service provider.

In accordance with another embodiment of the invention, a system for protecting the confidentiality of healthcare information may be provided. The system may include at least one memory and at least one processor. The at least one memory may be operable to store computer-executable instructions. The at least one processor may be configured to access the at least one memory and execute the computer-executable instructions to: receive, from a healthcare provider computer associated with a healthcare provider, a healthcare claim transaction; determine, based upon an analysis of the received healthcare claim transaction, identification information for a prescriber associated with the healthcare claim transaction; determine whether the identified prescriber is an at-risk prescriber that has previously failed to include appropriate directions for use in association with a prescription; and implement, if it is determined that the prescriber is an at-risk prescriber, a predetermined control action; or direct, if it is determined that the prescriber is not an at-risk prescriber, communication of the healthcare claim transaction to a claims processor computer associated with a claims processor.

Additional systems, methods, apparatus, features, and aspects may be realized through the techniques of various embodiments of the invention. Other embodiments and aspects of the invention are described in detail herein with reference to the description and to the drawings and are considered a part of the claimed invention.

BRIEF DESCRIPTION OF THE DRAWINGS

Reference will now be made to the accompanying drawings, which are not necessarily drawn to scale, and wherein.

DETAILED DESCRIPTION

Figure 1:
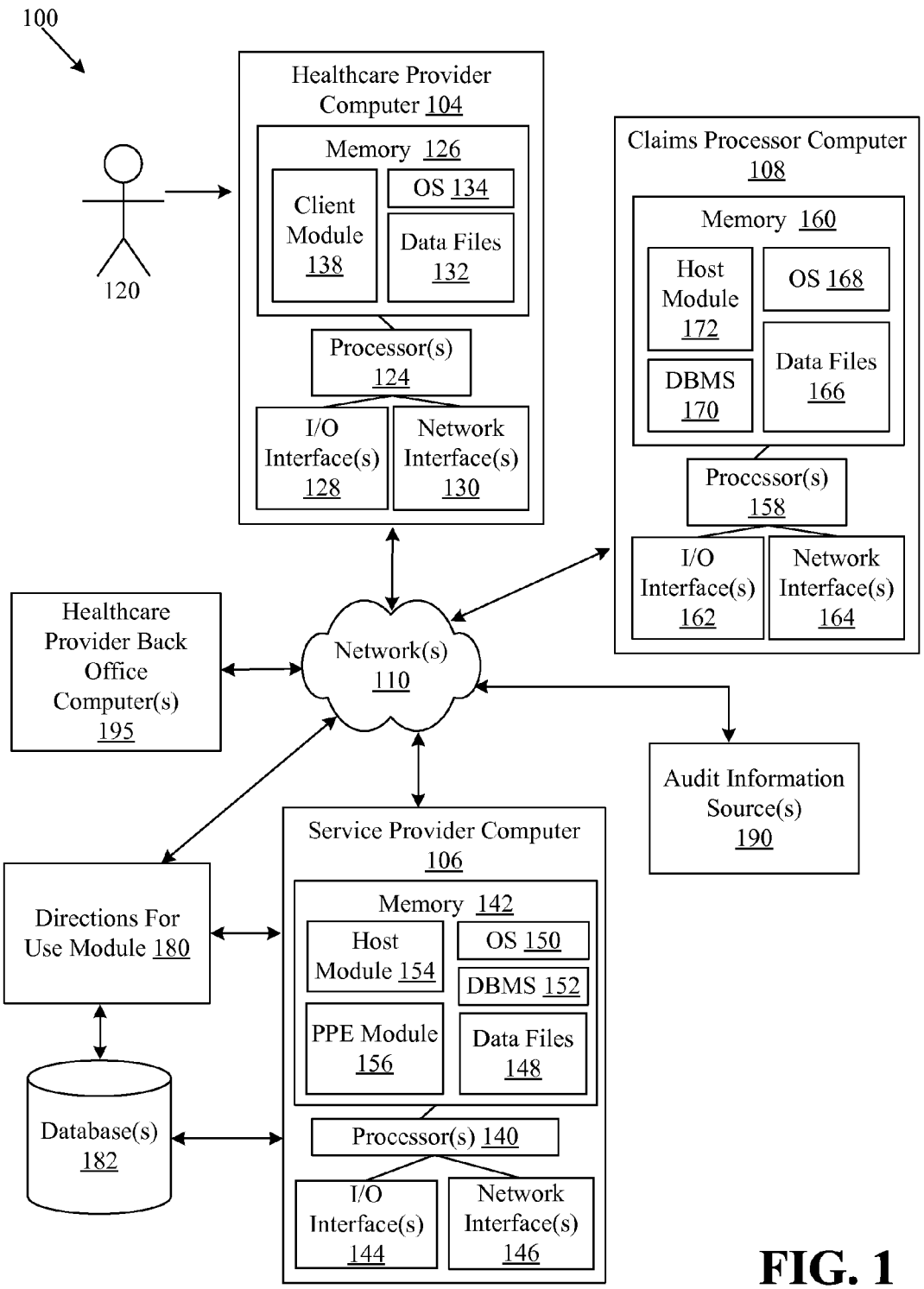
FIG. 1 illustrates an example overview of a system that may identify healthcare transactions having a risk of failing to include appropriate directions for use information, according to an example embodiment of the invention.

Embodiments of the invention now will be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Embodiments of the invention may include systems, methods, and apparatus for processing healthcare claim transactions in order to determine whether an underlying healthcare transaction has a risk of failing to include appropriate directions for use information. Directions for use information may include any suitable information associated with the dosage and/or proper therapeutic use of prescribed products. For example, directions for use information may include information specifying a dosage of a product to take and a number of times to take the product per day. In certain circumstances, a payer of healthcare benefits (e.g., an insurance company, etc.) may specify one or more parameters associated with required directions for use information. In the event that directions for use information provided by a prescriber fails to satisfy the one or more specified parameters, the payer may ultimately refuse to pay at least a portion of the costs associated with the prescribed product, and the payer may request another entity (e.g., a healthcare provider, etc.) to provide reimbursement for previously distributed funds.

In one example embodiment of the invention, a healthcare claim transaction may be received from a healthcare provider computer. For example, a healthcare claim transaction associated with one or more prescribed products may be received from a pharmacy computer or other healthcare provider computer. The received healthcare claim transaction may be evaluated or analyzed in order to identify a prescriber associated with the healthcare claim transaction and/or the prescribed one or more products. A determination may then be made as to whether the identified prescriber is an at-risk prescriber having an associated risk of failing to include appropriate or suitable directions for use information in prescriptions. If it is determined that the prescriber is not an at-risk prescriber, then the healthcare claim transaction may be communicated to an appropriate claims processor or adjudicator. If, however, it is determined that the prescriber is an at-risk prescriber, then a predetermined control action may be implemented. For example, a rejection for the healthcare claim transaction may be generated and returned to the healthcare provider computer. As another example, an indication that the prescriber is an at-risk prescriber may be generated, and the healthcare claim transaction may then be communicated to an appropriate claims processor.

A wide variety of suitable methods and/or techniques may be utilized in order to determine whether the identified prescriber is an at-risk prescriber. For example, prescriber identification information included in the healthcare claim transaction may be compared to information associated with at-risk prescribers, and the prescriber may be identified as an at-risk prescriber based at least in part upon a determined correspondence. In certain embodiments, the at-risk prescriber information may be information that is determined based upon an analysis of the results of one or more audits conducted on previous healthcare transactions. For example, audit information may be received from healthcare providers, claims processors, and/or other audit sources, and the audit information may be evaluated in order to identify healthcare transactions that were reversed and/or that resulted in chargebacks based upon a prescriber failing to include appropriate directions for use. Information associated with these healthcare transactions, such as prescriber identification information and/or prescribed product information, may be determined and stored in one or more databases of at-risk information. In this regard, information included in subsequently processed healthcare claim transactions may be evaluated in order to determine whether prescribers associated with the healthcare claim transactions are at-risk prescribers.

In certain embodiments, once a prescriber associated with a healthcare claim transaction has been identified, a determination may be made as to whether the identified prescriber is included in an inclusion list or an exclusion list. For example, a healthcare provider or a group of healthcare providers (e.g., a pharmacy chain, etc.) may provide an inclusion list that includes information associated with prescribers that should be identified as at-risk prescribers and/or an exclusion list that includes information associated with prescribers that should not be identified as at-risk prescribers. In the event that a prescriber associated with a healthcare claim transaction is determined to be included in an inclusion list, the prescriber may be identified as an at-risk prescriber. Similarly, if the prescriber is determined to be included in an exclusion list, then the prescriber may be identified as a prescriber that is not an at-risk prescriber.

As desired, other factors besides prescriber identification information may be evaluated in order to determine whether a prescriber is an at-risk prescriber. For example, a product associated with a healthcare claim transaction may be identified, and a determination may be made as to whether the identified product corresponds to stored product information associated with an at-risk prescriber. In the event that a product correspondence is identified, then the prescriber may be identified as an at-risk prescriber. In this regard, one or more products for which a prescriber typically fails to include appropriate directions for use information may be identified. An at-risk situation may then be identified based upon a determined correspondence between both prescriber information and product information with stored information. Additionally, as desired in various embodiments of the invention, inclusion and/or exclusion information may also be utilized in conjunction with product information. Other factors that may be evaluated include, but are not limited to, a refill factor and/or a number of times that a predetermined control action has been implemented. For example, an at-risk transaction may be identified for new prescriptions and refill transactions may be ignored. As another example, if a predetermined number of rejections (or other control action) has been implemented within a predetermined period of time (e.g., the previous hour, the previous day, etc.), then subsequent implementations of the control action may be suppressed. As desired, a different control action may be implemented. In this regard, an undesired number of rejections will not be provided to a healthcare provider, thereby improving workflow.

System Overview

An example system 100 that facilitates the identification of healthcare transactions having a risk of failing to include appropriate directions for use information will now be described with respect to FIG. 1. As shown in FIG. 1, the system 100 may include at least one healthcare provider computer 104, at least one service provider computer 106, and at least one claims processor computer 108. As desired, each of the healthcare provider computer 104, service provider computer 106, and/or claims processor computer 108 may include one or more processing devices that may be configured for accessing and reading associated computer-readable media having stored thereon data and/or computer-executable instructions for implementing the various methods of the invention.

Additionally, in certain embodiments, the service provider computer 106 may include or otherwise be in communication with a directions for use module 180 or directions for use application, which may access and/or be in communication with one or more suitable data storage devices and/or databases 182. The directions for use module 180 may evaluate healthcare claim transactions and determine whether a prescriber associated with the healthcare claim transaction is an at-risk prescriber having a risk of failing to include appropriate directions for use in conjunction with an underlying healthcare transaction. For example, the directions for use module 180 may evaluate the healthcare claim transaction in order to extract and/or identify a wide variety of different prescriber identification information associated with a prescriber. The prescriber identification information may then be compared to information associated with at-risk prescribers, and the prescriber may be identified as an at-risk prescriber based at least in part upon a determined correspondence. In this regard, corrective action may be taken by the directions for use module 180 in order to mitigate the risk of subsequent charge-backs and/or reimbursements that result in lost revenue on behalf of healthcare providers.

Generally, network devices and systems, including one or more of the healthcare provider computers 104, service provider computers 106, and/or claims processor computers 108 may include or otherwise be associated with suitable hardware and/or software for transmitting and receiving data, signals, and/or computer-executable instructions over one or more communications links or networks. As desired, these network devices and systems may also include any number of processors for processing data and executing computer-executable instructions, as well as other internal and peripheral components that are well-known in the art. Further, these network devices and systems may include or be in communication with any number of suitable memory devices operable to store data and/or computer-executable instructions. By executing computer-executable instructions, each of the network devices may form a special purpose computer or particular machine. As used herein, the term "computer-readable medium" describes any form of suitable memory or memory device.

As shown in FIG. 1, the healthcare provider computer 104, service provider computer 106, and claims processor computer 108 may be in communication with each other via one or more networks, such as networks 110, which as described below can include one or more separate or shared private and public networks, including the Internet and/or a public switched telephone network. Each of these components—the healthcare provider computer 104, the service provider computer 106, the claims processor computer 108, and the network 110—will now be discussed in further detail.

Each healthcare provider computer 104 may be associated with a respective pharmacy or other healthcare provider (e.g., a physician's office, a hospital, etc). In certain embodiments, a pharmacy may be associated with a group of pharmacies, such as a pharmacy chain. A healthcare provider computer 104 may be any suitable processor-driven device that facilitates the processing of healthcare requests made by patients or consumers and the communication of information associated with healthcare claim transactions to the service provider computer 106. For example, the healthcare provider computer 104 may be a server computer, a mainframe computer, one or more networked computers, a desktop computer, a personal computer, a digital assistant, a personal digital assistant, a digital tablet, an Internet appliance, an application-specific circuit, a microcontroller, a minicomputer, or any other processor-based device. In certain embodiments, the healthcare provider computer 104 may be a suitable point of sale device associated with a pharmacy. The execution of the computer-implemented instructions by the healthcare provider computer 104 may form a special purpose computer or other particular machine operable to facilitate the processing of healthcare requests made by patients and the communication of information associated with healthcare claim transactions to a service provider computer 106. Additionally, in certain embodiments of the invention, the operations and/or control of the healthcare provider computer 104 may be distributed among several processing components.

In addition to having one or more processors 124, the healthcare provider computer 104 may include one or more memory devices 126, one or more input/output ("I/O") interface(s) 128, and/or one or more network interface(s) 130. The memory devices 126 may be any suitable memory devices, for example, caches, read-only memory devices, random access memory devices, magnetic storage devices, removable storage devices, etc. The memory devices 126 may store data, executable instructions, and/or various program modules utilized by the healthcare provider computer 104, for example, data files 132, an operating system ("OS") 134, and/or a client module 138. The data files 132 may include any suitable data that facilitates the receipt and/or processing of healthcare requests by the healthcare provider computer 104, the generation and/or processing of healthcare claim transactions that are communicated to the service provider computer 106, and/or the receipt and/or processing of responses to various transactions and/or messages associated with various transactions. For example, the data files 132 may include, but are not limited to, healthcare information associated with one or more patients, information associated with the service provider computer 106, information associated with one or more claims processors, information associated with one or more healthcare claim transactions, and/or information associated with audits performed on prior healthcare claim transactions. The OS 134 may be a suitable software module that controls the general operation of the healthcare provider computer 104. The OS 134 may also facilitate the execution of other software modules by the one or more processors 124, for example, the client module 138. The OS 134 may be, but is not limited to, Microsoft Windows®, Apple OSX™, Linux, Unix, or a mainframe operating system. The client module 138 may be an Internet browser or other software, including a dedicated program, for interacting with the service provider computer 106. For example, a user 120, such as a pharmacist or other pharmacy employee, may utilize the client module 138 in preparing and providing a prescription claim request to the service provider computer 106 for delivery to the appropriate claims processor computer 108 for adjudication or other coverage/benefits determination. The healthcare provider computer 104 may also utilize the client module 138 to retrieve or otherwise receive data, messages, or responses from the service provider computer 106 and/or other components of the system 100.

In operation, the healthcare provider computer 104 may receive information associated with a healthcare request for a patient. As one example, the healthcare provider computer 104 may receive a healthcare request for a patient at a point of sale, such as in a pharmacy during a prescription fulfillment. As another example, the healthcare provider computer 104 may electronically receive a healthcare request from a patient computer or other patient device. The healthcare provider computer 104 may generate a healthcare claim transaction for the request, and information associated with the healthcare claim transaction may be communicated to the service provider computer 106. The healthcare provider computer 104 may then receive and process responses to the healthcare claim transaction, such as a rejection generated by the service provider computer 106 or an adjudicated reply generated by the claims processor computer 108.

The one or more I/O interfaces 128 may facilitate communication between the healthcare provider computer 104 and one or more input/output devices, for example, one or more user interface devices, such as a display, keypad, control panel, touch screen display, remote control, microphone, etc., that facilitate user interaction with the healthcare provider computer 104. For example, the one or more I/O interfaces 128 may facilitate entry of information associated with a healthcare transaction or a healthcare claim request by an employee 120 of a pharmacy. The one or more network interfaces 130 may facilitate connection of the healthcare provider computer 104 to one or more suitable networks, for example, the networks 110 illustrated in FIG. 1. In this regard, the healthcare provider computer 104 may receive and/or communicate information to other network components of the system 100, such as the service provider computer 106.

With continued reference to FIG. 1, the service provider computer 106 may include, but is not limited to, any suitable processor-driven device configured for receiving, processing, and fulfilling requests from the healthcare provider computer 104 and/or the claims processor computer 108 relating to prescriptions, pharmacy requests, benefits, healthcare transactions, therapeutic interchanges, and/or other activities. In certain embodiments, the service provider computer 106 may be a switch/router that routes healthcare claim transactions and/or other healthcare requests. For example, the service provider computer 106 may be configured to route billing requests and/or prescription claim requests communicated from the healthcare provider computer 104 to a claims processor computer 108, such as a pharmacy benefits manager ("PBM"), an insurer, a Medicare payer, another government payer, or a claims clearinghouse. In certain embodiments, the service provider computer 106 may include a suitable host server, host module, or other software that facilitates the receipt of a healthcare claim transaction from a healthcare provider computer 104 and/or the receipt of transaction responses from a claims processor computer 108. Any number of healthcare provider computers 104 and/or claims processor computers 108 may be in communication with the service provider computer 106 as desired in various embodiments of the invention.

The service provider computer 106 may include any number of special purpose computers or other particular machines, application-specific circuits, microcontrollers, personal computers, minicomputers, mainframe computers, servers, networked computers, and/or other processor-driven devices. In certain embodiments, the operations of the service provider computer 106 may be controlled by computer-executed or computer-implemented instructions that are executed by one or more processors associated with the service provider computer 106 to form a special purpose computer or other particular machine operable to facilitate receiving, routing, and/or processing of healthcare claim transactions. The one or more processors that control the operations of the service provider computer 106 may be incorporated into the service provider computer 106 and/or in communication with the service provider computer 106 via one or more suitable networks. In certain embodiments of the invention, the operations and/or control of the service provider computer 106 may be distributed among several processing components.

Similar to the healthcare provider computer 104, the service provider computer 106 may include one or more processors 140, one or more memory devices 142, one or more input/output ("I/O") interface(s) 144, and/or one or more network interface(s) 146. The one or more memory devices 142 may be any suitable memory devices, for example, caches, read-only memory devices, random access memory devices, magnetic storage devices, removable memory devices, etc. The one or more memory devices 142 may store data, executable instructions, and/or various program modules utilized by the service provider computer 106, for example, data files 148, an operating system ("OS") 150, the host module 154, a pre- and post-edit ("PPE") module 156, and a database management system ("DBMS") 152 to facilitate management of data files 148 and other data stored in the memory devices 142 and/or one or more databases 182. The OS 150 may be, but is not limited to, Microsoft Windows®, Apple OSX™, Linux, Unix, or a mainframe operating system. The OS 150 may be a suitable software module that controls the general operation of the service provider computer 106 and/or that facilitates the execution of other software modules.

The PPE module 156 may be operable to perform one or more pre-edits on a received healthcare claim transaction prior to routing or otherwise communicating the received healthcare claim transaction to a suitable claims processor computer 108. Additionally, the PPE module 156 may be operable to perform one or more post-edits on an adjudicated reply or response that is received from a claims processor computer 108 for a healthcare claim transaction prior to routing the adjudicated reply to the healthcare provider computer 104. A wide variety of different pre-edits and/or post-edits may be performed as desired in various embodiments of the invention. In certain embodiments, the directions for use module 180 may be incorporated into the PPE module 156 and/or in communication with the PPE module 156. For example, a directions for use service provided by the directions for use module 180 may be implemented as a pre-edit. As another example, the directions for use service may be implemented following the execution of pre-edits performed by the PPE module 156.

According to an embodiment of the invention, the data files 148 may store healthcare transaction records associated with communications received from various healthcare provider computers 104 and/or various claims processor computers 108. The data files 148 may also store any number of suitable routing tables that facilitate determining the destination of communications received from a healthcare provider computer 104 or a claims processor computer 108. The host module 154 may receive, process, and respond to requests from the client module 138 of the healthcare provider computer 104, and may further receive, process, and respond to requests of the host module 172 of the claims processor computer 108. The service provider computer 106 may include additional program modules for performing other processing methods described herein. Those of ordinary skill in the art will appreciate that the service provider computer 106 may include alternate and/or additional components, hardware or software without departing from example embodiments of the invention.

A directions for use module 180 or directions for use application may also be operative with the service provider computer 106. The directions for use module 180 may include computer-executable instructions for evaluating healthcare claim transactions to determine whether a prescriber is an at-risk prescriber having a risk of failing to provide appropriate directions for use in conjunction with a prescription or underlying healthcare transaction. In this regard, the directions for use module 180 may identify situations that may result in future charge-backs and/or reimbursements in the event that the healthcare claim transaction is audited. As a result, additional action may be taken by healthcare providers in order to ensure that appropriate directions for use are provided, thereby mitigating the risk of future charge-backs and/or reimbursements that may result in lost profits.

In operation, the directions for use module 180 may receive information associated with a healthcare claim transaction. The directions for use module 180 may evaluate the received information in order to identify a wide variety of different parameters, such as prescriber identification information (e.g., a National Provider Identifier ("NPI"), another prescriber identifier, a prescriber name, etc.) and/or identification information for one or more prescribed products (e.g., a National Drug Code ("NDC"), a product name, etc.). The identified parameters and/or other information may then be processed by the directions for use module 180 in order to determine whether the prescriber is an at-risk prescriber.

A wide variety of suitable methods and/or techniques may be utilized by the directions for use module 180 in order to determine whether the identified prescriber is an at-risk prescriber. For example, prescriber identification information included in the healthcare claim transaction (e.g., an NPI, etc.) may be compared to information associated with at-risk prescribers, such as stored information associated with at-risk prescribers. A determination may then be made as to whether the prescriber identification information corresponds to at least a portion of the information associated with at-risk prescribers. In the event that a correspondence is identified, the prescriber may be identified as an at-risk prescriber.

In certain embodiments, the at-risk prescriber information may be information identified and/or determined by the directions for use module 180 based upon an analysis of the results of one or more audits conducted on previous healthcare transactions. For example, audit information may be received from a wide variety of different sources, such as the healthcare provider computer 104, a healthcare provider back office computer 195, the claims processor computer 108, and/or one or more audit information sources 190. In certain embodiments, the directions for use module 180 may request the audit information from another entity. In other embodiments, the audit information may be "pushed" to the directions for use module 180 and/or the service provider computer 106 by another entity. Additionally, in certain embodiments, the received audit information may be evaluated by the directions for use module 180 in order to identify healthcare transactions that were reversed and/or that resulted in charge-backs based upon a prescriber failing to include appropriate directions for use. In other embodiments, only audit information associated with transactions that failed to include appropriate directions for use may be received by the directions for use module 180. During the processing of audit results, information associated with healthcare transactions that failed to include appropriate directions for use, such as prescriber identification information and/or prescribed product information, may be determined by the directions for use module 180 and stored in one or more databases 182 of at-risk information. In this regard, information included in subsequently processed healthcare claim transactions may be evaluated in order to determine whether prescribers associated with the subsequently processed healthcare claim transactions are at-risk prescribers.

Additionally, in certain embodiments, the directions for use module 180 may utilize one or more prescriber inclusion and/or exclusion lists to determine whether a prescriber is an at-risk prescriber. As desired, an inclusion and/or exclusion list may be received from a wide variety of different sources, such as the healthcare provider computer 104 and/or the healthcare provider back office computer 195. Alternatively, default lists may be utilized. Once a prescriber associated with a healthcare claim transaction has been identified by the directions for use module 180, a determination may be made as to whether the identified prescriber is included in an inclusion list or an exclusion list. In the event that the prescriber is determined to be included in an inclusion list, then the prescriber may be automatically identified by the directions for use module 180 as an at-risk prescriber. Similarly, if the prescriber is determined to be included in an exclusion list, then the prescriber may be identified by the directions for use module 180 as a prescriber that is not an at-risk prescriber.

As desired, other factors besides prescriber identification information may be evaluated by the directions for use module 180 in order to determine whether a prescriber is an at-risk prescriber. For example, a product associated with a healthcare claim transaction may be identified by the directions for use module 180, and a determination may be made as to whether the identified product corresponds to stored product information associated with an at-risk prescriber. For example, product information may be extracted from the received audit information and stored in association with at-risk prescriber information. In this regard, one or more products for which a prescriber typically fails to include appropriate directions for use information may be identified. In the event that a product correspondence is identified by the directions for use module 180, then the prescriber may be identified as an at-risk prescriber. Otherwise, the prescriber may be identified as a prescriber that is not an at-risk prescriber. Additionally, as desired in various embodiments of the invention, inclusion and/or exclusion information may also be utilized in conjunction with product information. These product inclusion and/or exclusion lists may be similar to the prescriber inclusion and/or exclusion lists discussed above.

Other factors that may be evaluated by the directions for use module 180 include, but are not limited to, a refill factor and/or a number of times that a predetermined control action has been implemented. For example, an at-risk transaction may be identified for new prescriptions while refill transactions may be ignored. As another example, the directions for use module 180 may track a number of times that control actions and/or corrective actions (e.g., a healthcare transaction rejection, etc.) have been implemented on behalf of a healthcare provider. Following the identification of a prescriber as an at-risk prescriber, the directions for use module 180 may evaluate one or more tolerance parameters for taking various control actions. In certain embodiments, these tolerance parameters may be provided by the healthcare provider computer 104 or the healthcare provider back office computer 195. One example tolerance parameter or threshold parameter may establish a predetermined number of times that a control action may be implemented within a given period of time (e.g., the previous hour, the previous day, etc.). Once a prescriber has been identified as an at-risk prescriber, the directions for use module 180 may determine whether a tolerance parameter or threshold has been met or satisfied. If the tolerance parameter has not been satisfied, then the directions for use module 180 may implement a control action. However, if the tolerance parameter has been satisfied, then the directions for use module 180 may suppress the control action that would normally be implemented. As desired, a different control action may be implemented by the directions for use module 180. For example, the generation of a rejection may be suppressed, and an at-risk notification may be generated and stored instead. As a result of evaluating tolerance parameters and/or thresholds, the number of rejections generated by the directions for use module 180 may be controlled and/or limited, thereby reducing the work performed by healthcare provider employees and improving healthcare provider workflow.

In certain embodiments, if the directions for use module 180 determines that a prescriber associated with a healthcare claim transaction is not an at-risk prescriber, then the directions for use module 180 may mark the healthcare claim transaction as suitable for routing to an appropriate claims processor or adjudicator. If, however, the directions for use module 180 determines that the prescriber is an at-risk prescriber, then an exception may be identified and/or generated by the directions for use module 180. The directions for use module 180 may then take a wide variety of suitable control actions based upon the identified exception. In certain embodiments, one or more exception processing parameters may be evaluated in order to identify an appropriate control action to take based at least in part upon the identified exception. For example, profile information associated with healthcare providers and/or groups of healthcare providers may be evaluated in order to identify exception processing parameters. A desired control action may then be identified and implemented.

A wide variety of control actions may be implemented by the directions for use module 180 as desired in various embodiments of the invention. For example, in certain embodiments, a rejection for the healthcare claim transaction may be generated by the directions for use module 180, and the generated rejection may be returned to the healthcare provider computer 104. As desired, the generated rejection may include a wide variety of suitable information, such as an indication that the prescriber was identified as an at-risk prescriber, an instruction to verify that appropriate directions for use are included in a prescription, and/or an invitation to resubmit the healthcare claim transaction once the verification has been completed. As another example of a suitable control action, an indication may be generated that the prescriber associated with the healthcare claim transaction has a risk of failing to provide appropriate directions for use. As desired, the indication may be communicated to a wide variety of different recipients, such as the healthcare provider computer 104 and/or the healthcare provider back office computer 195. Additionally or alternatively, the indication may be stored for subsequent reporting purposes. Following the generation of the indication, the directions for use module 180 may mark the healthcare claim transaction as appropriate for communication to an appropriate claims processor. The control actions described above are provided by way of example only, and other control actions may be utilized as desired in various embodiments of the invention.

Additionally, as desired, the directions for use module 180 may store or direct the storage of information associated with the processing of healthcare claim transactions in the databases or data storage devices 182. For example, the directions for use module 180 may store information associated with received healthcare claim transactions, information associated with identified exceptions and/or at-risk transactions, information associated with rules applied by the directions for use module 180, information associated with generated rejections, and/or information associated with at-risk transactions that have been routed to claims processors. In certain embodiments, the stored information may be utilized for billing and/or reporting purposes. For example, the directions for use module 180 may utilize at least a portion of the stored information to bill pharmacies and/or pharmacy chains for the services provided by the directions for use module 180.

The data storage devices 182 may be operable to store information associated with various rules, parameters, and/or edits that may be utilized by the directions for use module 180. For example, rules may be received from one or more other components of the system 100, such as the healthcare provider computer 104, the healthcare provider back office computer 195, and/or the claims processor computer 108, and at least a portion of the received rules may be stored. The data storage devices 182 may also store audit information, information associated with at-risk prescribers and/or associated prescribed products, and/or information associated with inclusion and/or exclusion lists. Additionally, the data storage devices 182 may be operable to store information associated with healthcare claim transactions and/or processing performed by the directions for use module 180. In certain embodiments, the data storage devices 182 may additionally store billing information associated with the healthcare claim transactions and/or reports associated with the healthcare claim transactions and/or processing of the healthcare claim transactions. As desired, the data storage devices 182 may be accessible by the directions for use module 180 and/or the service provider computer 106.

In certain embodiments, the directions for use module 180 and/or the service provider computer 106 may be operable to generate one or more reports associated with processed healthcare claim transactions. A wide variety of different types of reports may be generated as desired in various embodiments of the invention. Additionally, a wide variety of different information may be incorporated into generated reports including, but not limited to, a number of times the directions for use module 180 was invoked for a healthcare provider or chain of healthcare providers, information associated with the results of various processing performed by the directions for use module 180, date information and/or date range information associated with processed healthcare claim transactions, financial information associated with the healthcare claim transactions, and/or billing information associated with the invocation of the directions for use module 180. Reports may be sorted or formatted utilizing a wide variety of different criteria, parameters, and/or techniques. Additionally, the directions for use module 180 may communicate or direct the communication of generated reports to one or more other components of the system, for example, the healthcare provider computer 104 and/or a healthcare provider back office computer 195.

A wide variety of different techniques and/or software programs may be utilized to format a generated report. For example, a report may be formatted as a comma-separated-value ("csv") file, as a spreadsheet file, as a word processor file, as a text file, etc. Additionally, a wide variety of different communication techniques may be utilized to communicate a report to the recipient including, but not limited to, email, short message service ("SMS") messaging, other electronic communications, snail mail, etc. A report may be pushed to a recipient by the directions for use module 180 or other reporting module, or alternatively pulled from the directions for use module 180 by a recipient submitting a request for one or more reports. Additionally, in certain embodiments, a report may be made available for download from an appropriate Web site or server, such as a Web site hosted by the service provider computer 106.

One example of the operations of the directions for use module 180 and/or the data storage devices 182 is described in greater detail below with reference to FIGS. 3-5.

With continued reference to the service provider computer 106, the one or more I/O interfaces 144 may facilitate communication between the service provider computer 106 and one or more input/output devices, for example, one or more user interface devices, such as a display, keypad, control panel, touch screen display, remote control, microphone, etc., that facilitate user interaction with the service provider computer 106. The one or more network interfaces 146 may facilitate connection of the service provider computer 106 to one or more suitable networks, for example, the networks 110 illustrated in FIG. 1. In this regard, the service provider computer 106 may communicate with other components of the system 100.

With continued reference to FIG. 1, the claims processor computer 108 may be any suitable processor-driven device that facilitates receiving, processing, and/or fulfilling healthcare claim transactions and/or healthcare claim requests received from the service provider computer 106. For example, the claims processor computer 108 may be a processor-driven device associated with a pharmacy benefits manager ("PBM"), an insurer, a Medicare payer, another government payer, or a claims clearinghouse. As desired, the claims processor computer 108 may include any number of special purpose computers or other particular machines, application-specific circuits, microcontrollers, personal computers, minicomputers, mainframe computers, servers, and the like. In certain embodiments, the operations of the claims processor computer 108 may be controlled by computer-executed or computer-implemented instructions that are executed by one or more processors associated with the claims processor computer 108 to form a special purpose computer or other particular machine that is operable to facilitate the receipt, processing, and/or fulfillment of healthcare claim transaction requests received from the service provider computer 106. The one or more processors that control the operations of the claims processor computer 108 may be incorporated into the claims processor computer 108 and/or in communication with the claims processor computer 108 via one or more suitable networks. In certain embodiments of the invention, the operations and/or control of the claims processor computer 108 may be distributed among several processing components.

Similar to other components of the system 100, the claims processor computer 108 may include one or more processors 158, one or more memory devices 160, one or more input/output ("I/O") interface(s) 162, and/or one or more network interface(s) 164. The one or more memory devices 160 may be any suitable memory devices, for example, caches, read-only memory devices, random access memory devices, magnetic storage devices, removable memory devices, etc. The one or more memory devices 160 may store data, executable instructions, and/or various program modules utilized by the claims processor computer 108, for example, data files 166, an operating system ("OS") 168, a database management system ("DBMS") 170, and a host module 172. The data files 166 may include any suitable information that is utilized by the claims processor computer 108 to process healthcare claim transactions, for example, patient profiles, patient Medicare eligibility and/or insurance information, other information associated with a patient, information associated with a healthcare provider, etc. The OS 168 may be a suitable software module that controls the general operation of the claims processor computer 108. The OS 168 may also facilitate the execution of other software modules by the one or more processors 158, for example, the DBMS 170 and/or the host module 172. The OS 168 may be, but is not limited to, Microsoft Windows®, Apple OSX™, Linux, Unix, or a mainframe operating system. The DBMS 170 may be a suitable software module that facilitates access and management of one or more databases that are utilized to store information utilized by the claims processor computer 108 in various embodiments of the invention. The host module 172 may initiate, receive, process, and/or respond to requests, such as healthcare claim transactions or claim requests, from the host module 154 of the service provider computer 106. The claims processor computer 108 may include additional program modules for performing other pre-processing or post-processing methods described herein. Those of ordinary skill in the art will appreciate that the claims processor computer 108 may include alternate and/or additional components, hardware or software without departing from example embodiments of the invention.

The one or more I/O interfaces 162 may facilitate communication between the claims processor computer 108 and one or more input/output devices, for example, one or more user interface devices, such as a display, keypad, control panel, touch screen display, remote control, microphone, etc. that facilitate user interaction with the claims processor computer 108. The one or more network interfaces 164 may facilitate connection of the claims processor computer 108 to one or more suitable networks, for example, the network 110 illustrated in FIG. 1. In this regard, the claims processor computer 108 may receive healthcare claim transactions and/or other communications from the service provider computer 106, and the claims processor computer 108 may communicate information associated with processing claim transactions to the service provider.

With continued reference to FIG. 1, any number of audit information sources 190 may be provided. Each of the audit information sources 190 may be configured to store audit result information associated with audits performed on adjudicated healthcare claim transactions and/or underlying healthcare transactions. Additionally, each of the audit information sources 190 may be configured to provide stored information to the service provider computer 106 and/or the directions for use module 180. In certain embodiments, a directions for use module 180 may be associated with a claims processor and/or payer. Additionally, each of the audit information sources 190 may be a suitable processor-driven device that includes components similar to other devices included in the system 100, such as the healthcare provider computer 104. For example, an audit information source 190 may include at least one memory, at least one processor, one or more I/O interfaces, and/or one or more network interfaces. As desired, an audit information source 190 may include software and/or computer-executable instructions that may be executed to facilitate the provision of audit information to the directions for use module 180 and/or the service provider computer 106. For example, in certain embodiments, the audit information source 190 may receive requests for audit information from the directions for use module 180, and the audit information source 190 may return audit information to the directions for use module 180 in response to the received requests. In other embodiments, the directions for use module 180 may periodically (or based upon the identification of an event, such as a change or update of information) push or otherwise communicate audit information to the directions for use module 180 for storage in the databases 182. For example, the audit information source 190 may communicate audit information to the directions for use module 180 once a day, once a week, once a month, etc. In yet other embodiments, the audit information source 190 may communicate updated or new audit information to the directions for use module 180. In addition to or as an alternative to obtaining audit information from one or more audit information sources, the directions for use module 180 and/or the service provider computer 106 may obtain audit information from one or more other entities, such as the claims processor computer 108, the healthcare provider computer 104, and/or the healthcare provider back office computer 195.

With continued reference to FIG. 1, the healthcare provider back office computer 195 may be one or more computers associated with a group of healthcare providers, such as a group of pharmacies. The healthcare provider back office computer 195 may include components similar to other devices included in the system 100, such as the healthcare provider computer 104. For example, the healthcare provider back office computer 195 may be a processor-driven device that includes at least one memory, at least one processor, one or more I/O interfaces and/or one or more network interfaces. The healthcare provider back office computer 195 may further include software and/or computer-executable instructions that may be executed by the at least one processor to receive reports and/or billing information associated with the processing of healthcare claim transactions by the directions for use module 180. Additionally, as desired, the healthcare provider back office computer 195 may be operable or configured to provide various rules, parameters, and/or preferences associated with processing healthcare claim transactions to the service provider computer 106 and/or the directions for use module 180. For example, the healthcare provider back office computer 195 may provide inclusion and/or exclusion lists for prescribers and/or products to the service provider computer 106 and/or the directions for use module 180.

The networks 110 may include any number of telecommunication and/or data networks, whether public, private, or a combination thereof, including a local area network, a public switched telephone network, a wide area network, an intranet, the Internet, intermediate handheld data transfer devices, and/or any combination thereof and may be wired and/or wireless. For example, the networks 110 may include a public switched telephone network that facilitates telephone communication between various devices within the system 100.

Due to network connectivity, various methodologies as described herein may be practiced in the context of distributed computing environments. Although the service provider computer 106 is shown for simplicity as being in communication with the healthcare provider computers 104 and/or the claims processor computers 108 via one intervening network 110, it is to be understood that any other network configuration is possible. For example, intervening network 110 may include a plurality of networks, each with devices such as gateways and routers for providing connectivity between or among networks 110. Instead of or in addition to a network 110, dedicated communication links may be used to connect the various devices in accordance with an example embodiment of the invention. For example, the service provider computer 106 may form the basis of network 110 that interconnects the healthcare provider computer 104 and the claims processor computer 108.

Those of ordinary skill in the art will appreciate that the system 100 shown in and described with respect to FIG. 1 is provided by way of example only. Numerous other operating environments, system architectures, and device configurations are possible. Other system embodiments can include fewer or greater numbers of components and may incorporate some or all of the functionality described with respect to the system components shown in FIG. 1. For example, in one embodiment, the service provider computer 106 (or other computer) may be implemented as a specialized processing machine that includes hardware and/or software for performing the methods described herein. In addition, at least a portion of the processor and/or processing capabilities of the service provider computer 106 and/or the directions for use module 180 may be implemented as part of the claims processor computer 108 or the healthcare provider computer 104. Accordingly, embodiments of the invention should not be construed as being limited to any particular operating environment, system architecture, or device configuration.

Operational Overview

Figure 2A:
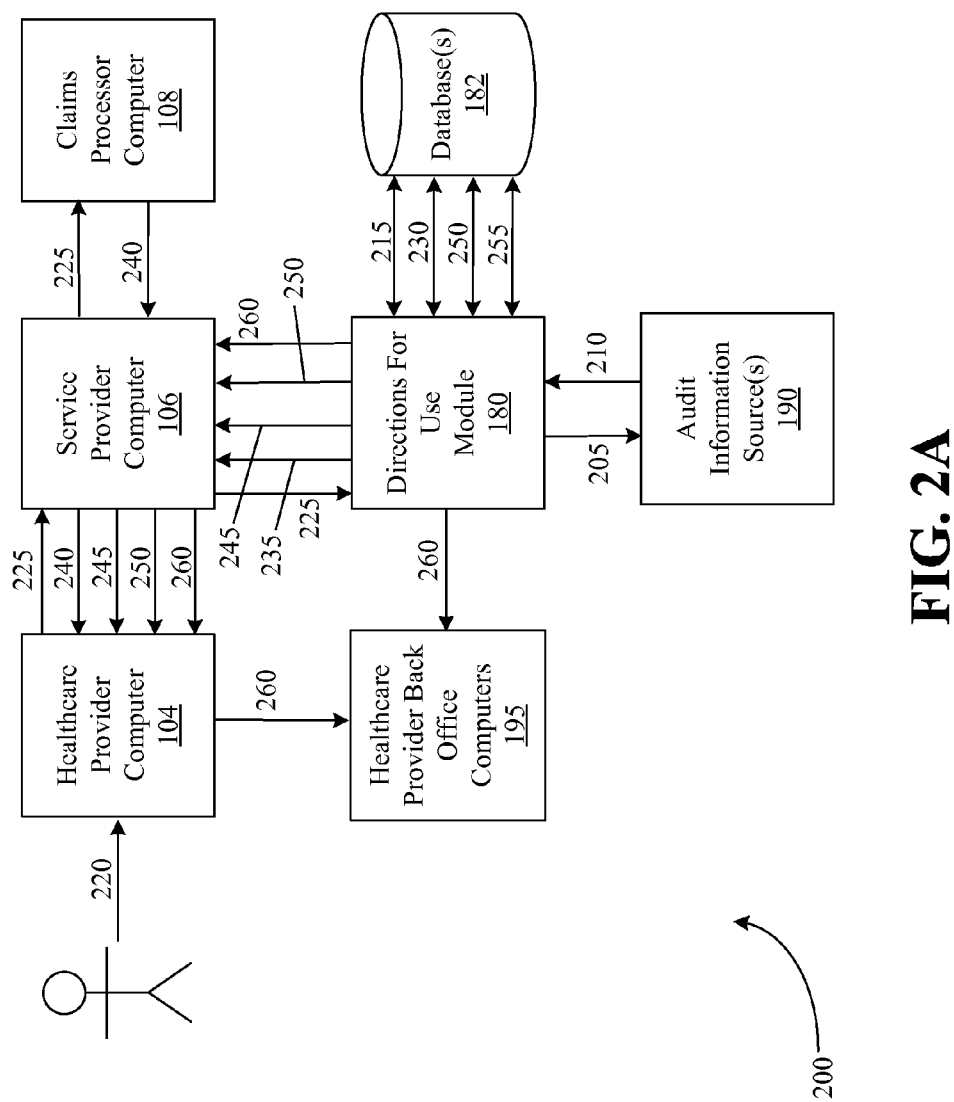
FIGS. 2A-2B are block diagrams of example data flows for evaluating healthcare claim transactions as the transactions are processed through a service provider, according to illustrative embodiments of the invention.

FIG. 2A is a block diagram of one example data flow 200 for evaluating healthcare claim transactions as the healthcare claim transactions are processed through a service provider, such as the service provider computer 106 illustrated in FIG. 1. With reference to FIG. 2A, a suitable directions for use module, such as the directions for use module 180 illustrated in FIG. 1, may be configured to identify information associated with at-risk prescribers of healthcare products. In other words, the directions for use module 180 may identify one or more prescribers having a risk of failing to include directions for use information on prescriptions. In certain embodiments, the directions for use module 180 may identify at-risk prescribers based upon an evaluation of audit information associated with previously adjudicated healthcare transactions. This audit information may be obtained from a wide variety of different entities. For example, with reference to FIG. 1, the directions for use module 180 may generate one or more requests 205 for audit information, and the generated requests may be communicated to any number of respective audit information sources, such as the audit information sources 190 illustrated in FIG. 1. Audit information 210 may then be received from the audit information sources 190 in response to the requests. Alternatively, audit information 210 may be received from the audit information sources 190 without the audit information 210 being requested. Although the audit information 210 is described as being received from the audit information sources 190, audit information 210 may additionally or alternatively be received from a wide variety of other entities, such as a healthcare provider or a claims processor.

Once the audit information 210 has been received, the directions for use module 180 may analyze and/or evaluate the received audit information 210. In doing so, the directions for use module 180 may identify one or more prior healthcare transactions that have been reversed and/or that resulted in charge-backs or reimbursements based upon a prescriber failing to include appropriate directions for use information. Additionally, a wide variety of at-risk information 215 associated with the healthcare transactions may be determined, such as identification information for the prescribers (e.g., NPI codes, other prescriber identifiers, prescriber names, etc.) and/or identification information for one or more prescribed products (e.g., NDC information, product names, etc.) for which appropriate directions for use were not provided. Once determined, the at-risk information 215 may be stored in one or more suitable databases accessible by the directions for use module 180, such as the databases 182 illustrated in FIG. 1.

With continued reference to FIG. 2A, a healthcare request 220, such as a request for a prescription drug or other medication product, may be received by a healthcare provider computer 104 from a patient. The healthcare request 220 may be received in-person or electronically as desired in various embodiments of the invention. For example, a patient may present a prescription to request a product at a pharmacy, and a pharmacy employee may enter information associated with the request into the healthcare provider computer 104. As another example, a patient may communicate a healthcare request 220 and/or prescription information to a healthcare provider computer 104 via one or more suitable network connections. For example, a purchase request for a prescription product may be communicated to a healthcare provider computer 104 from a customer computer via a Web portal hosted by the healthcare provider computer 104.

The healthcare provider computer 104 may receive and process the healthcare request 220 to generate a healthcare claim transaction 225, such as a healthcare claim request or a prescription claim request, and the healthcare claim transaction 225 may be communicated by the healthcare provider computer 104 to the service provider computer 106. According to an example embodiment of the invention, the healthcare claim transaction 225 may be in accordance with a version of a National Council for Prescription Drug Programs ("NCPDP") Telecommunication Standard, although other standards may be utilized as well. As desired, the healthcare claim transaction 225 may include a Banking Identification Number ("BIN") and/or a Processor Control Number ("PCN") for identifying a particular claims processor computer or payer, such as the claims processor computer 108 illustrated in FIG. 1, as a destination for the healthcare claim transaction 225. In addition, the healthcare claim transaction 225 may also include information relating to the patient, payer, prescriber, pharmacy, and/or product. As an example, the healthcare claim transaction 225 received by the service provider computer 106 may include one or more of the following information:

- Payer ID/Routing Information
  - BIN Number (i.e. Banking Identification Number) and/or Processor Control Number (PCN) that designates a destination of the healthcare claim transaction
- Patient Information
  - Name (e.g., Patient Last Name, Patient First Name, etc.)
  - Date of Birth of Patient
  - Age of Patient
  - Gender
  - Patient Address (e.g., Street Address, Zip Code, etc.)
  - Patient Contact Information (e.g., Patient Telephone Number, email address, etc.)
  - Patient ID or other identifier
- Insurance/Coverage Information
  - Cardholder Name (e.g., Cardholder First Name, Cardholder Last Name)
  - Cardholder ID and/or other identifier (e.g., person code)
  - Group ID and/or Group Information
  - State Payer Information
  - Prescriber Information
  - Primary Care Provider ID or other identifier (e.g., National Provider Identifier (NPI) code)
  - Primary Care Provider Name (e.g., Last Name, First Name)
  - Prescriber ID or other identifier (e.g., NPI code, Drug Enforcement Agency (DEA) number)
  - Prescriber Name (e.g., Last Name, First Name)
  - Prescriber Contact Information (e.g., Telephone Number)
  - Pharmacy or other Healthcare Provider Information (e.g., store name, chain identifier, etc.)
  - Pharmacy or other Healthcare Provider ID (e.g., NPI code)
- Claim Information
  - Drug or product information (e.g., National Drug Code (NDC))
  - Prescription/Service Reference Number
  - Date Prescription Written
  - Quantity Dispensed
  - Number of Days Supply
  - Diagnosis/Condition
  - Pricing information for the drug or product (e.g., network price, Usual & Customary price)
  - One or more NCPDP Message Fields
  - One or more Drug Utilization Review (DUR) Codes
  - One or more Dispense as Written (DAW) Codes
  - Date of Service.

With continued reference to FIG. 2A, the service provider computer 106 may receive the healthcare claim transaction 225 from the healthcare provider computer 104, and the service provider computer 106 may process the healthcare claim transaction 225. As desired, the service provider computer 106 may perform one or more pre-edits on the healthcare claim transaction 225. The pre-edits may evaluate, verify, add, and/or edit information included in the healthcare claim transaction 225 prior to the healthcare claim transaction 225 being communicated to an appropriate claims processor computer 108. In certain embodiments, a determination may be made as to whether a directions for use edit or directions for use service is enabled for the healthcare claim transaction 225. For example, a determination may be made as to whether a healthcare provider or a group of healthcare providers associated with the healthcare claim transaction 225 has enabled or activated a directions for use service for implementation in processing healthcare claim transactions that are routed or otherwise communicated through the service provider computer 106. If a directions for use service has not been enabled, then the healthcare claim transaction 225 and/or a copy thereof may be routed or otherwise communicated by the service provider computer 106 to an appropriate claims processor computer 108 associated with a designated payer for adjudication. According to an example embodiment, the service provider computer 106 may utilize at least a portion of the information included in the healthcare claim transaction 225, such as a BIN/PCN, to determine the appropriate claims processor computer 108 for routing. The service provider computer 106 may also include a routing table, perhaps stored in memory, for determining which claims processor computer 108 to route the healthcare claim transaction 225 to. The claims processor computer 108 may receive and adjudicate or otherwise process the healthcare claim transaction 225. For example, the claims processor computer 108 may determine benefits coverage for the healthcare claim transaction 225 according to an adjudication process associated with eligibility, pricing, and/or utilization review. The claims processor computer 108 may transmit an adjudicated reply 240 or response for the healthcare claim transaction 225 to the service provider computer 106. The service provider computer 106 may receive the adjudicated reply 240 from the claims processor computer 108. As desired, the service provider computer 106 may perform any number of post-edits on the adjudicated reply 240. The adjudicated reply 240 or a copy thereof may then be routed or otherwise communicated to the healthcare provider computer 104.

However, if a directions for use edit has been enabled, then the healthcare claim transaction 225 or a copy thereof may be communicated to the directions for use module 180 for processing. The directions for use module 180 may evaluate the healthcare claim transaction 225 and determine whether a prescriber associated with the healthcare claim transaction 225 is a prescriber that is at-risk for failing to provide appropriate directions for use information. For example, the directions for use module 180 may analyze the healthcare claim transaction 225 to determine identification information for a prescriber (e.g., a NPI, a prescriber name, etc.) and/or identification information for one or more prescribed products (e.g., NDC codes, product names, etc.). The directions for use module 180 may then determine whether the identified prescriber is an at-risk prescriber.

In certain embodiments, the directions for use module 180 may access at least a portion of the stored at-risk information 215, and the directions for use module 180 may determine whether the prescriber is an at-risk prescriber based at least in part upon comparing prescriber and/or product information to accessed at-risk information 215. Additionally, as desired in various embodiments, the directions for use module 180 may access one or more inclusion lists and/or exclusion lists 230 that specify prescribers and/or products to be included and/or excluded from an at-risk determination. The directions for use module 180 may determine whether a prescriber and/or a product is included in one or more relevant inclusion lists and/or exclusion lists 230, and the directions for use module 180 may determine whether the prescriber is an at-risk prescriber based at least in part upon the determination of whether the prescriber and/or product is included in one or more relevant lists 230. For example, if prescriber information and/or product information corresponds to stored prescriber and/or product information included in one or more inclusion lists, then the prescriber may be identified as an at-risk prescriber. Similarly, if prescriber information and/or product information corresponds to stored prescriber and/or product information included in one or more exclusion lists, then the prescriber may be identified as a prescriber that is not an at-risk prescriber.

If the directions for use module 180 determines that a prescriber associated with the healthcare claim transaction 225 is not an at-risk prescriber, then the directions for use module 180 may generate an instruction 235 to route or communicate the healthcare claim transaction 225 to the claims processor computer 108. The generated instruction 235 may be communicated to the service provider computer 106, and the service provider computer 106 may route or otherwise communicate the healthcare claim transaction 225 to the claims processor computer 108 for adjudication. An adjudicated reply 240 may then be received by the service provider computer 106 from the claims processor computer 108, and the received adjudicated reply 240 may be routed or otherwise communicated to the healthcare provider computer 104.

If, however, the directions for use module 180 determines that a prescriber associated with the healthcare claim transaction 225 is an at-risk prescriber, then the directions for use module 180 may implement a suitable control action with respect to the healthcare claim transaction 225. In certain embodiments, a control action to be implemented may be determined based at least in part upon an evaluation of one or more parameters associated with a healthcare provider that submitted the healthcare claim transaction 225. A wide variety of different control actions may be implemented by the directions for use module 180 as desired in various embodiments of the invention. For example, in certain embodiments, the directions for use module 180 may generate a rejection 245 associated with the healthcare claim transaction 225. The rejection 245 may include a wide variety of different information, such as an indication that the healthcare claim transaction 225 has been rejected because the prescriber is an at-risk prescriber, an instruction to verify that appropriate directions for use have been provided by the prescriber, and/or an invitation to resubmit the healthcare claim transaction 225 following the verification. Once generated, the rejection 245 may be communicated by the directions for use module 180 to the service provider computer 106, and the service provider computer 106 may communicate the rejection 245 to the healthcare provider computer 104.

As another example control action, the directions for use module 180 may determine that an automatic rejection will not be generated. For example, the directions for use module 180 may determine that a rejection threshold has been reached and/or that the healthcare provider does not wish to receive rejections. Accordingly, the directions for use module 180 may generate an instruction 235 to route or communicate the healthcare claim transaction 225 to the claims processor computer 108. The generated instruction 235 may be communicated to the service provider computer 106, and the service provider computer 106 may route or otherwise communicate the healthcare claim transaction 225 to the claims processor computer 108 for adjudication. Additionally, as desired, the directions for use module 180 may generate an indication 250 that a directions for use exception has been identified and/or that the prescriber has been identified as an at-risk prescriber. As desired, the generated indication 250 may be stored in the databases 182 for subsequent reporting purposes. Additionally, as desired, the generated indication 250 may be provided to the service provider computer 106 for communication to the healthcare provider computer 104.

In certain embodiments of the invention, the directions for use module 180 may store information 255 associated with the processed healthcare claim transaction 225 for reporting and/or billing purposes. A wide variety of information 255 may be stored as desired in various embodiments of the invention, for example, a copy of the healthcare claim transaction 225, information extracted from the healthcare claim transaction 225, information associated with the processing of the directions for use module 180, information associated with identified at-risk prescriber exceptions, information associated with implemented control actions, information associated with generated rejections and/or indications, etc. In certain embodiments, information associated with invocation of the directions for use module 180 may be communicated to an appropriate billing system associated with the service provider computer 106 in order to facilitate billing customers, such as healthcare providers, for the services provided by the directions for use module 180. Alternatively, the directions for use module 180 may alter a billing code or other field of the healthcare claim transaction 225 to a value indicating that the healthcare claim transaction 225 has been evaluated or processed by the directions for use module 180. The altered billing code may be recognized during subsequent or further processing of the healthcare claim transaction 225, such as further processing by the service provider computer 106, in order to facilitate billing.

According to another aspect of the invention, the directions for use module 180 or a reporting system associated with the directions for use module 180 and/or service provider computer 106 may utilize at least a portion of stored information 255 to generate one or more reports 260 that include information associated with the processing of the healthcare claim transaction 225. The generation of reports is discussed in greater detail above with respect to FIG. 1. As desired, generated reports 260 may be communicated to customers of the service provider or to customer systems and/or devices, for example, the healthcare provider computer 104 and/or to the healthcare provider back office computer 195. A wide variety of suitable communications techniques, for example, electronic mail, short message service ("SMS") messaging, other electronic communications, snail mail, etc., may be utilized as desired to communicate generated reports to one or more recipients.

Figure 2B:
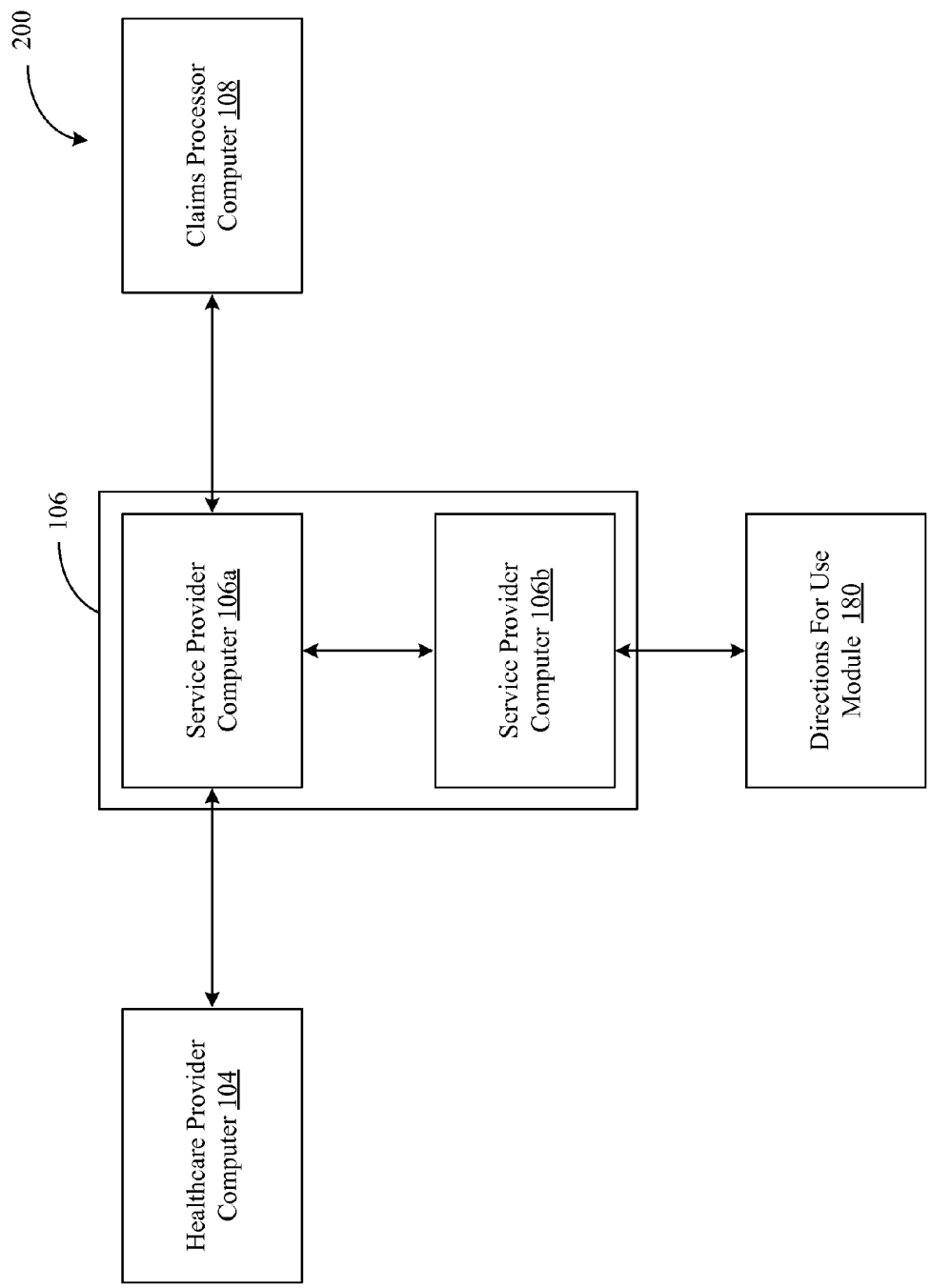

It will be appreciated that variations of the data flow 200 illustrated in FIG. 2A may be utilized in accordance with various embodiments of the invention. For example, as shown in FIG. 2B, the service provider computer 106 may be comprised of two or more distinct service provider computers 106a and 106b that are in communication with each other. Service provider computer 106a may be operative with one or more healthcare provider computers and claims processor computers, such as the healthcare provider computer 104 and the claims processor computer 108 illustrated in FIG. 1. However, service provider computer 106b may have a data processing arrangement with service provider computer 106a. Under the data processing agreement, the service provider computer 106a may be permitted to utilize or offer services of the service provider computer 106b, including those of the directions for use module 180. For example, a first service provider may communicate healthcare claim transactions to a second service provider for processing.

As described herein, healthcare claim transactions may be examined as they are routed to or through a service provider computer 106. In this regard, a directions for use service may be provided in real-time or near real-time as various transactions are routed to or through the service provider computer 106. FIG. 3 is a flow diagram of an example method 300 for processing a healthcare claim transaction, according to an illustrative embodiment of the invention. The method 300 may be performed by a suitable service provider computer and/or an associated directions for use module, such as the service provider computer 106 and the directions for use module 180 illustrated in FIG. 1. The method 300 may begin at block 305.

At block 305, information associated with one or more at-risk prescribers may be identified. For example, audit information may be received and/or otherwise obtained, and the audit information may be evaluated in order to identify one or more healthcare transactions that were reversed and/or that resulted in charge-backs as a result of failing to include appropriate directions for use information. Prescriber information and/or prescribed product information associated with the identified healthcare transaction may then be determined, and at least a portion of the prescriber information and/or product information may be stored and/or maintained in an at-risk prescriber database. One example of the operations that may be performed to identified information associated with one or more at-risk prescribers is described in greater detail below with reference to FIG. 4.

At block 310, a healthcare claim transaction may be received from a healthcare provider computer, such as the healthcare provider computer 104 shown in FIG. 1. One or more pre-edits and/or evaluations may be performed on the received healthcare claim transaction as desired in various embodiments of the invention. For example, one or more pre-edits may be performed by a PPE module associated with the service provider computer 106, such as the PPE module 156 shown in FIG. 1. At block 315, a determination may be made as to whether a directions for use service or directions for use edit has been enabled and/or activated for a healthcare provider that submitted the healthcare claim transaction or for a group or chain to which the healthcare provider belongs. For example, processing parameters for the healthcare provider or group of healthcare providers (e.g., pharmacy chain) may be analyzed in order to determine whether a directions for use service has been enabled. If it is determined at block 315 that a directions for use service has not been enabled, then operations may continue at block 320. At block 320, the healthcare claim transaction may be routed or otherwise communicated to a suitable claims processor computer, such as the claims processor computer 108 illustrated in FIG. 1, for adjudication. Any received adjudicated reply for the healthcare claim transaction may then be routed or otherwise communicated to the healthcare provider computer 104. Operations may end following block 320.

If, however, it is determined at block 315 that a directions for use service has been enabled, then operations may continue at block 325. At block 325, the healthcare claim transaction may be processed utilizing the directions for use service. For example, the healthcare claim transaction may be processed by the directions for use module 180 or directions for use application. The directions for use module 180 may determine whether a prescriber associated with the healthcare claim transaction is an at-risk prescriber having an associated risk of failing to provide appropriate directions for use information. One example of the operations that may be performed by the directions for use module 180 in order to evaluate or process the healthcare claim transaction is described in greater detail below with reference to FIGS. 5A and 5B.

At block 330, a determination may be made as to whether one or more exceptions have been generated by the directions for use module 180. For example, a determination may be made as to whether the directions for use module 180 has generated an exception identifying a prescriber associated with the healthcare claim transaction as an at-risk prescriber. If it is determined at block 330 that one or more exceptions have not been generated, then operations may continue at block 320, and the healthcare claim transaction may be routed or otherwise communicated to the claims processor computer 108 for adjudication. Operations may then either end or optionally continue at block 340 (not shown). If, however, it is determined at block 330 that one or more exceptions have been generated, then operations may continue at block 335. At block 335, one or more suitable or appropriate control actions associated with the exception(s) may be implemented. For example, a rejection may be generated for the healthcare claim transaction, and the rejection may be returned to the healthcare provider computer 104. As another example, an indication of an exception may be communicated to the healthcare provider computer 104 while the healthcare claim transaction is permitted to be routed or otherwise communicated to the claims processor computer 108.

At block 340, which may be optional in certain embodiments of the invention, information associated with the healthcare claim transaction and/or the invocation of the directions for use module 180 may be stored and/or communicated for billing and/or reporting purposes. As explained in greater detail above, a wide variety of information may be stored in various embodiments of the invention. As desired in certain embodiments, billing information may be communicated to a suitable billing system associated with the service provider. In other embodiments, billing information may be stored for subsequent access by a billing system or for subsequent access by another component of the service provider for communication to the billing system. Billing information may be utilized by the billing system in order to charge customers of the service provider for the directions for use service provided by the directions for use module 180. A wide variety of different types of billing information may be stored and/or communicated as desired in various embodiments of the invention, for example, an identifier associated with the invocation of the directions for use module 180 or a billing code (e.g., a unique billing code) associated with the invocation of the directions for use module 180. As an alternative to storing or communicating billing information, the directions for use module 180 may set a billing code for the healthcare claim transaction to a unique billing code associated with the provided directions for use service. The unique billing code may be identified or recognized during subsequent processing of the healthcare claim transaction by either the billing system or a component of the service provider computer 106. The identified billing code may then be utilized by the billing system in the generation of bills for customers of the service provider.

At block 345, which may be optional in certain embodiments of the invention, one or more reports may be generated utilizing at least a portion of the stored information. For example, reports may be generated by the directions for use module 180, the service provider computer 106, and/or a separate reporting module. As described in greater detail above, a wide variety of different information may be included in a generated report. Additionally, generated reports may be formatted and/or sorted utilizing a wide variety of different parameters and/or criteria, such as identifiers for healthcare provider computers, identifiers for healthcare providers, identifiers for prescribers, identifiers for products associated with healthcare claim transactions, dates of service, etc. As desired, generated reports may be communicated to one or more recipients, such as the healthcare provider computer 104 and/or a healthcare provider back office computer, such as the healthcare provider back office computer 195 illustrated in FIG. 1.

The method 300 may end following either block 320 or block 345.

Figure 3:
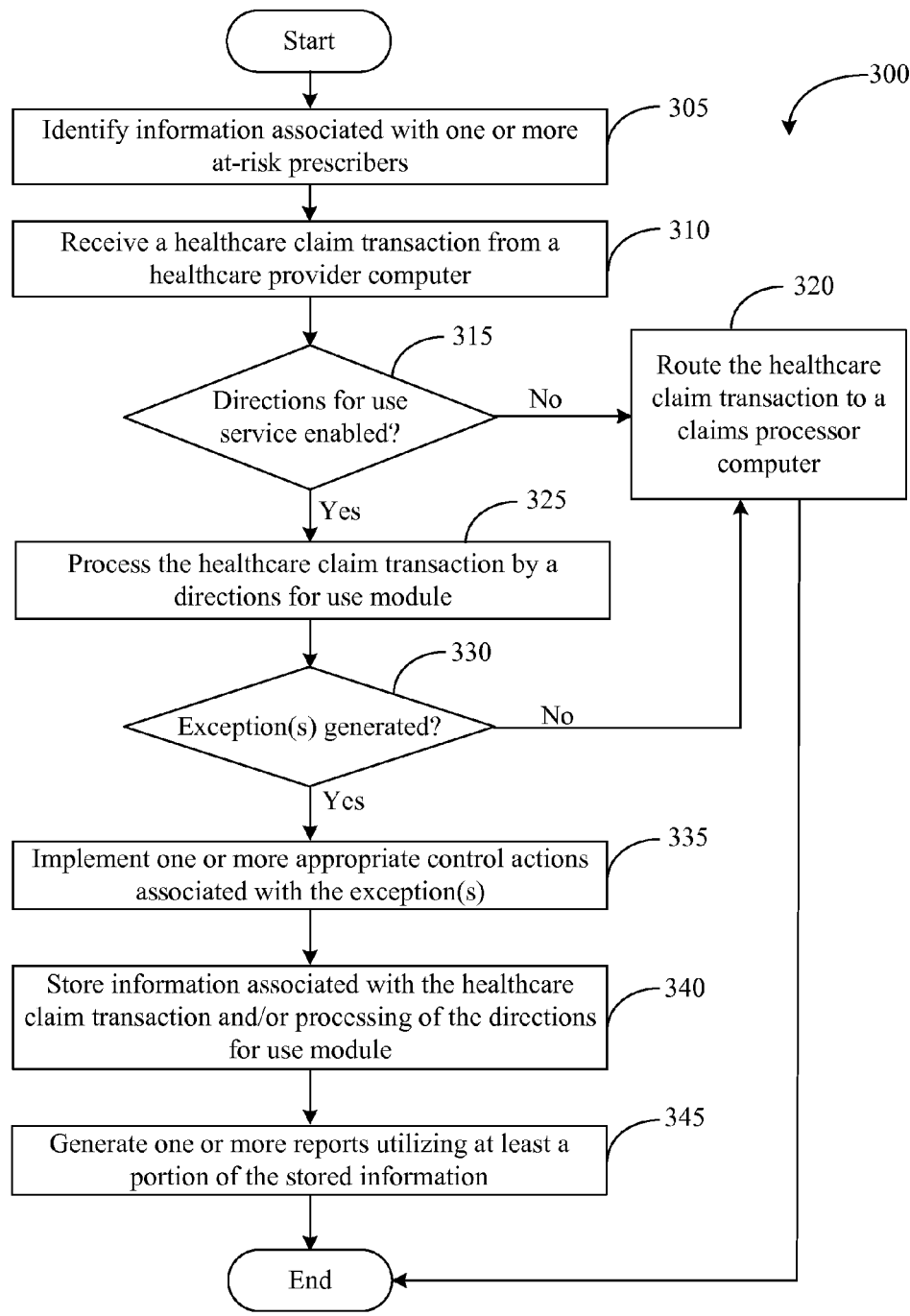
FIG. 3 is a flow diagram of an example method for processing healthcare claim transactions, according to an illustrative embodiment of the invention.
Figure 4:
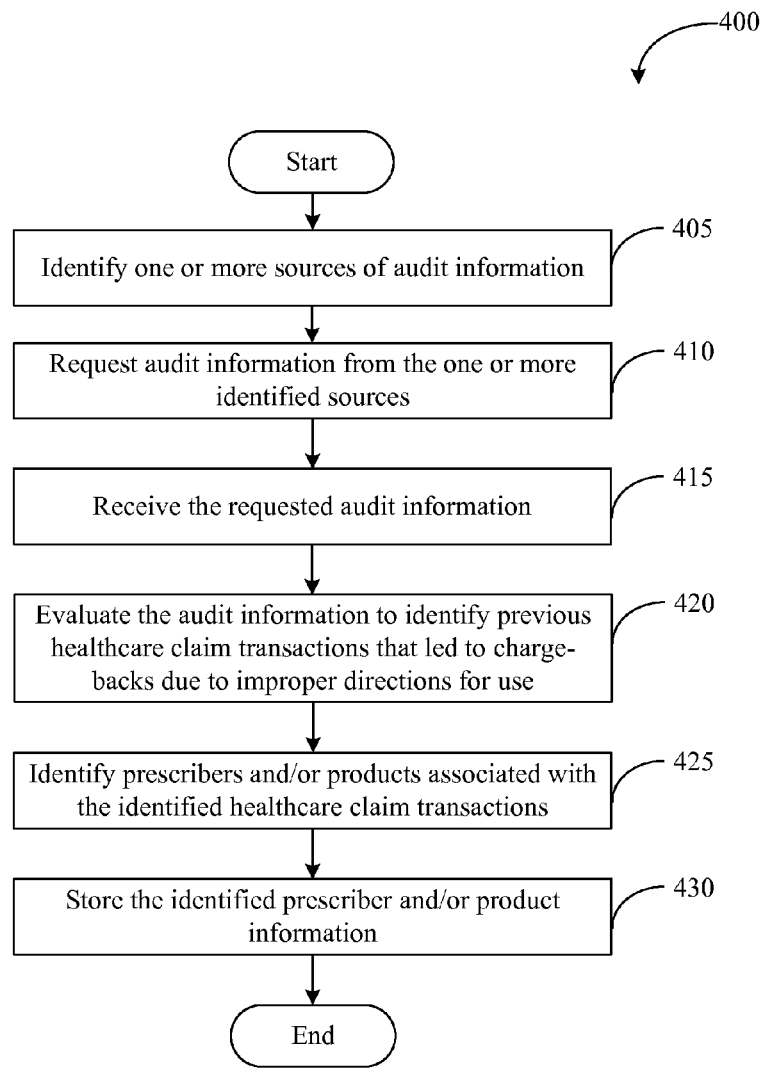
FIG. 4 is a flow diagram of an example method for identifying and/or storing information associated with prescribers that have an associated risk of failing to include appropriate directions for use, according to an illustrative embodiment of the invention.

FIG. 4 is a flow diagram of an example method 400 for identifying and/or storing information associated with prescribers that have an associated risk of failing to include appropriate directions for use, according to an illustrative embodiment of the invention. In other words, FIG. 4 illustrates an example method 400 for identifying information associated with at-risk prescribers. The method 400 of FIG. 4 is one example of the operations that may be implemented at block 305 shown in FIG. 3. As such, the method 400 may be performed by a suitable service provider computer and/or directions for use module, such as the service provider computer 106 and/or the directions for use module 180 illustrated in FIG. 1. The method 400 may begin at block 405.

At block 405, one or more sources of audit information may be identified. For example, one or more payers, claims processors, healthcare providers, and/or independent auditing entities that have conducted audits on healthcare claim transactions and/or that have the results of audits may be identified as potential sources of audit information. At block 410, audit information may be requested from one or more of the identified sources of audit information. For example, one or more requests for audit information may be generated, and the generated requests may be communicated to one or more of the identified audit information sources. A wide variety of information may be included in a request as desired in various embodiments of the invention, such as identification information for one or more healthcare providers associated with desired audit information and/or a request for audit information associated with transactions that resulted in charge-backs and/or reimbursements based at least in part upon an audit determination that appropriate directions for use information was not provided by a prescriber.

At block 415, at least a portion of the requested audit information may be received from one or more audit information sources. As an alternative to receiving audit information in response to a request, audit information may be communicated by an audit information source to the service provider computer 106 and/or the directions for use module 180 without the information being requested. In other words, an audit information source may "push" audit information to the service provider. Additionally, as desired in certain embodiments of the invention, a service provider associated with the directions for use module 180 may conduct audits on one or more healthcare transactions, and the results of the audits may be provided to the directions for use module 180.

At block 420, received, accessed, and/or otherwise obtained audit information may be evaluated in order to identify adjudicated healthcare claim transactions and/or underlying healthcare transactions that led to charge-backs or reimbursements due to prescribers failing to provide appropriate directions for use information in conjunction with prescriptions. In certain embodiments, received and/or accessed audit information may only include audit information for transactions that failed to include appropriate directions for use information. In other embodiments, audit information may be sorted, evaluated, and/or analyzed in order to identify relevant healthcare transactions. For example, one or more reason codes and/or comment fields may be searched in order to identify relevant healthcare transactions.

At block 425, the identified relevant healthcare transactions may be evaluated in order to identify information associated with at-risk prescribers. For example, identification information for the prescribers associated with the relevant healthcare transactions (e.g., NPI codes, other prescriber identifiers, prescriber names, etc.) may be determined. Additionally, as desired, identification information for one or more prescribed products (e.g., NDC codes, other product identifiers, product names, etc.) associated with the relevant healthcare transactions may be determined. In this regard, one or more products for which respective prescribers fail to provide appropriate directions for use may be identified and associated with the prescribers. As desired in various embodiments of the invention, respective payer and/or claims processor information associated with the relevant healthcare transactions may also be identified. Different payers may have different requirements for including directions for use information. Accordingly, payers having a relatively higher risk of auditing and/or requesting a charge-back may be identified.

At block 430, at least a portion of the determined information may be stored in one or more suitable databases, such as the databases 182 illustrated in FIG. 2. For example, prescriber and/or product identification information associated with at-risk prescribers may be stored. In this regard, at least a portion of the information may be subsequently accessed in order to evaluate healthcare claim transactions that are being communicated through the service provider computer 106. As desired, payer information may also be stored. In this regard, at least a portion of the payer information may be accessed during the processing of the evaluated healthcare claim transactions.

The method 400 may end following block 430.

Figure 5A:
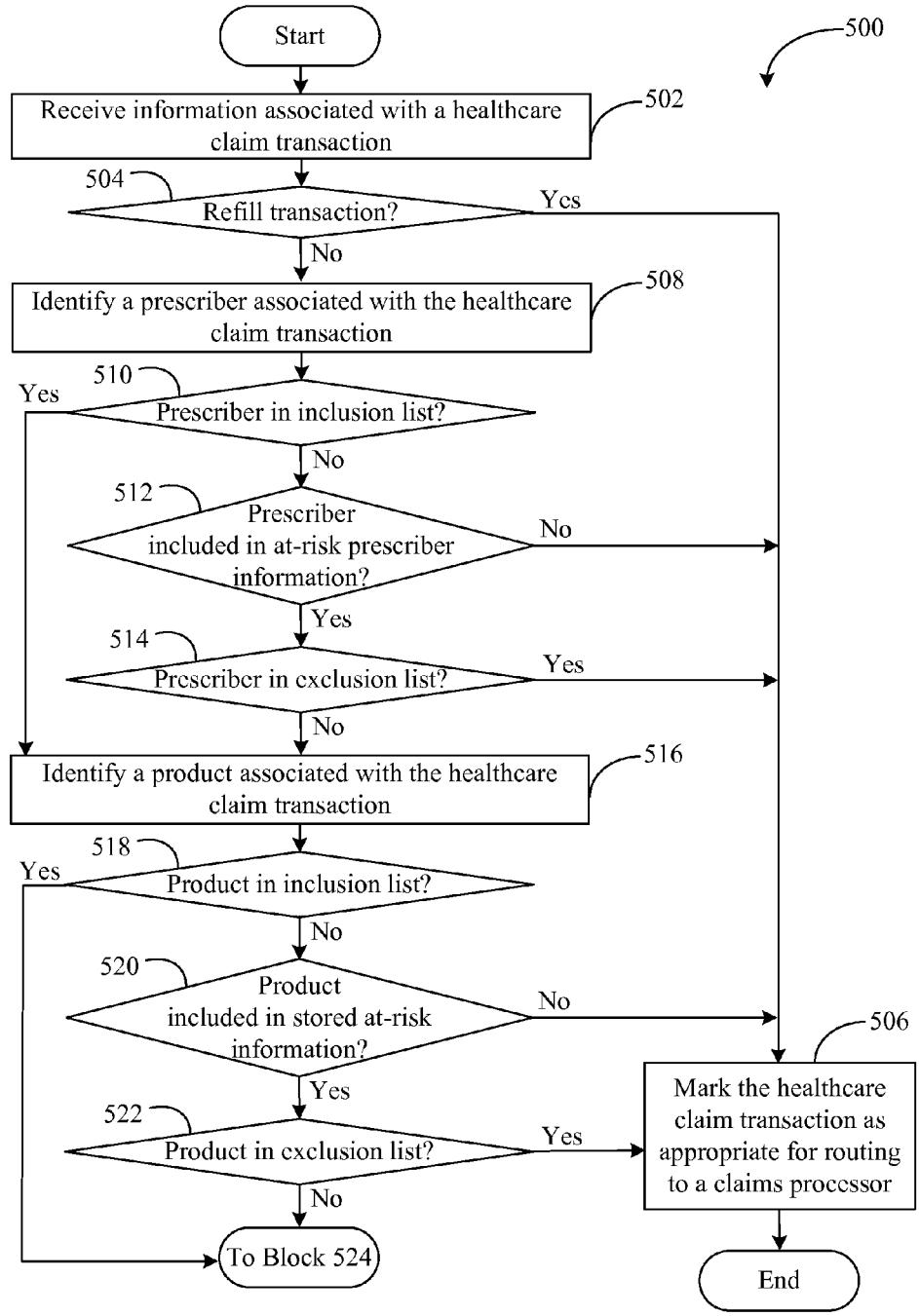
FIGS. 5A and 5B illustrate a flow diagram of an example method for processing a healthcare claim transaction to determine whether a risk of failing to include appropriate directions for use is associated with the healthcare claim transaction, according to an illustrative embodiment of the invention.
Figure 5B:
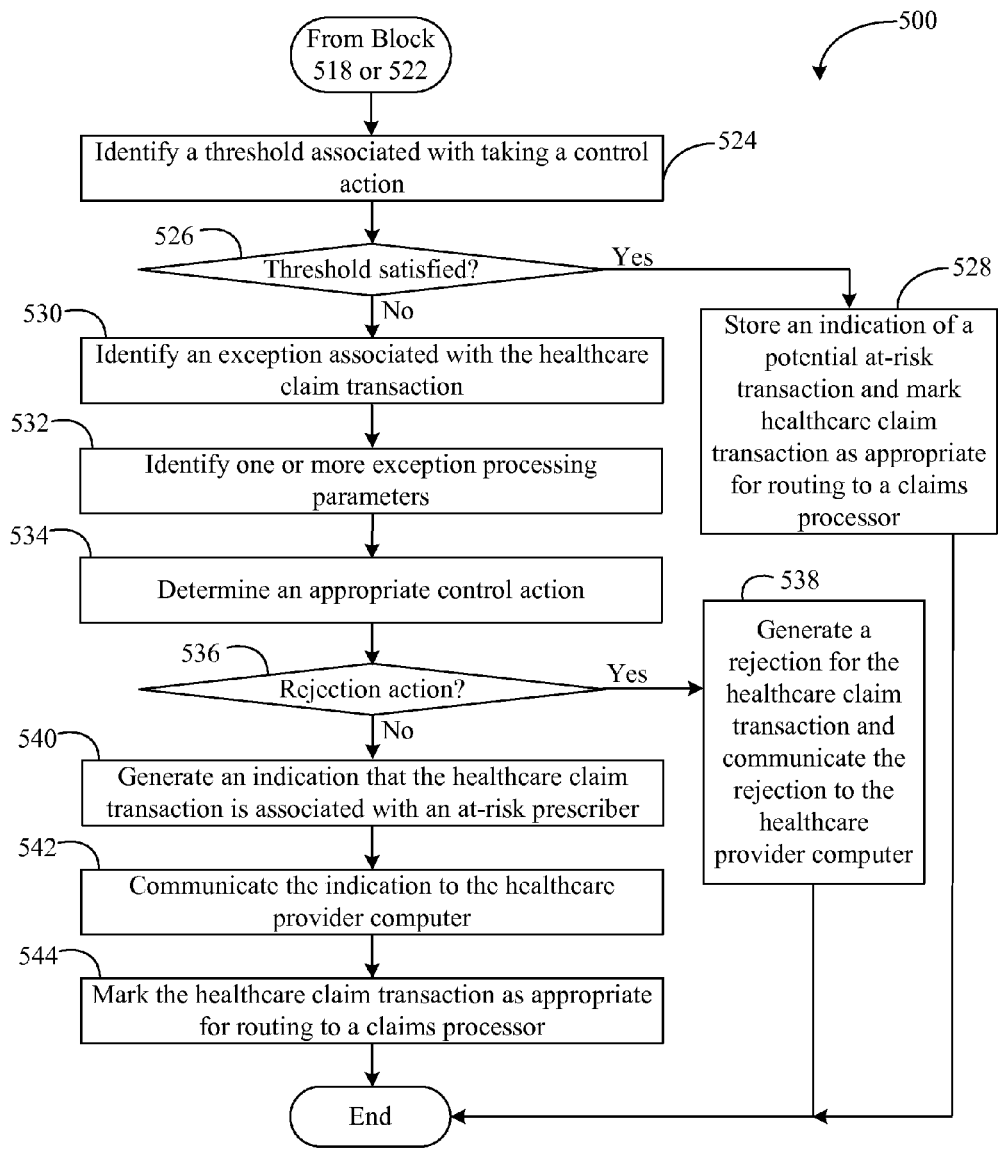

FIGS. 5A and 5B illustrate a flow diagram of an example method 500 for processing a healthcare claim transaction to determine whether a risk of failing to include appropriate directions for use is associated with the healthcare claim transaction, according to an illustrative embodiment of the invention. The method 500 illustrated in FIGS. 5A and 5B may be an example implementation of block 325 shown in FIG. 3. As such, the method 500 may be performed by a suitable service provider computer and/or directions for use module, such as the service provider computer 106 and/or the directions for use module 180 illustrated in FIG. 1. The method 500 may begin at block 502.

At block 502, information associated with a healthcare claim transaction may be received. For example, a copy of the healthcare claim transaction or information extracted from the healthcare claim transaction may be received. In this regard, a suitable directions for use service may be performed with respect to the healthcare claim transaction. In certain embodiments, a determination may be made as to whether override information is included in the healthcare claim transaction to facilitate suppression of the directions for use service. For example, a determination may be made as to whether an override code is provided in conjunction with a resubmission of a previously rejected healthcare claim transaction. If override information is provided, then operations may end. Otherwise, a directions for use service may be performed.

At block 504, a determination may be made as to whether the healthcare claim transaction is a refill transaction. In other words, a determination may be made as to whether the healthcare claim transaction is associated with a refill request for one or more prescribed products. A wide variety of suitable methods and/or techniques may be utilized as desired to determine whether the transaction is a refill transaction. For example, a fill number included in the healthcare claim transaction may be evaluated in order to determine a number of times that a prescription has been filled. If it is determined at block 504 that the healthcare claim transaction is a refill transaction, then operations may continue at block 506, and the healthcare claim transaction may be marked as suitable for routing to an appropriate claims processor. If, however, it is determined at block 504 that the healthcare claim transaction is not a refill transaction, then operations may continue at block 508.

At block 508, a prescriber associated with the healthcare claim transaction may be identified. For example, the healthcare claim transaction may be evaluated in order to determine a wide variety of different prescriber identification information, such as a National Provider Identifier ("NPI") code or a prescriber name. At block 510, a determination may be made as to whether the identified prescriber is included in a prescriber inclusion list. For example, at least a portion of a prescriber inclusion list associated with a healthcare provider (or group of healthcare providers) that submitted the healthcare claim transaction may be accessed. Identification information for the identified prescriber may be compared to information included in the prescriber inclusion list, and a determination may be made as to whether a correspondence exists. For example, a determination may be made as to whether an NPI code for the prescriber matches an NPI code included in the prescriber inclusion list. If it is determined at block 510 that the identified prescriber is included in a prescriber inclusion list, then operations may continue at block 516 described in greater detail below. If, however, it is determined at block 510 that the identified prescriber is not included in a prescriber inclusion list, then operations may continue at block 512.

At block 512, a determination may be made as to whether the identified prescriber is a prescriber included in at-risk prescriber information. For example, one or more repositories or databases of at-risk prescriber information, such as information stored as a result of evaluating audit information, may be accessed. Identification information for the identified prescriber may be compared to the at-risk prescriber information, and a determination may be made as to whether a correspondence exists. For example, a determination may be made as to whether an NPI code for the prescriber matches an NPI code included in the at-risk prescriber information. If it is determined at block 512 that the identified prescriber is not a prescriber included in the at-risk prescriber information, then operations may continue at block 506, and the healthcare claim transaction may be marked as suitable for routing to an appropriate claims processor. If, however, it is determined at block 512 that the identified prescriber is a prescriber included in the at-risk prescriber information, then operations may continue at block 514.

At block 514, a determination may be made as to whether the identified prescriber is included in a prescriber exclusion list. For example, at least a portion of a prescriber exclusion list associated with a healthcare provider (or group of healthcare providers) that submitted the healthcare claim transaction may be accessed. Identification information for the identified prescriber may be compared to information included in the prescriber exclusion list, and a determination may be made as to whether a correspondence exists. If it is determined at block 514 that the identified prescriber is a prescriber included in the prescriber exclusion list, then operations may continue at block 506, and the healthcare claim transaction may be marked as suitable for routing to an appropriate claims processor. If, however, it is determined at block 514 that the identified prescriber is not a prescriber included in the prescriber exclusion list, then operations may continue at block 516.

At block 516, a product (e.g., a prescribed product) associated with the healthcare claim transaction may be identified. For example, the healthcare claim transaction may be evaluated in order to determine a wide variety of different product identification information, such as a National Drug Code ("NDC") or a product name. At block 518, a determination may be made as to whether the identified product is included in a product inclusion list. For example, at least a portion of a product inclusion list associated with a healthcare provider (or group of healthcare providers) that submitted the healthcare claim transaction may be accessed. In certain embodiments, the product inclusion list may include product information applicable to all prescribers. In other embodiments, the product inclusion list may include respective product information for one or more specified prescribers. Identification information for the identified product may be compared to information included in the product inclusion list, and a determination may be made as to whether a correspondence exists. For example, a determination may be made as to whether an NDC code for the product matches an NDC code included in the product inclusion list. If it is determined at block 518 that the identified product is included in a product inclusion list, then operations may continue at block 524 described in greater detail below. If, however, it is determined at block 518 that the identified product is not included in a product inclusion list, then operations may continue at block 520.

At block 520, a determination may be made as to whether the identified product is a product included in accessed at-risk information. For example, one or more repositories or databases of at-risk information, such as information stored as a result of evaluating auditing information, may be accessed. In certain embodiments, the accessed at-risk information may include product information applicable to all prescribers, such as information associated with products for which prescribers typically fail to include directions for use information and/or typically provide inappropriate directions for use information. In other embodiments, the accessed at-risk information may include respective product information associated with one or more at-risk prescribers. Identification information for the identified product may be compared to the at-risk product information, and a determination may be made as to whether a correspondence exists. For example, a determination may be made as to whether an NDC code for the product matches an NDC code included in the at-risk product information. If it is determined at block 520 that the identified product is not a product included in the at-risk information, then operations may continue at block 506, and the healthcare claim transaction may be marked as suitable for routing to an appropriate claims processor. If, however, it is determined at block 520 that the identified product is a product included in the at-risk information, then operations may continue at block 522.

At block 522, a determination may be made as to whether the identified product is included in a product exclusion list. For example, at least a portion of a product exclusion list associated with a healthcare provider (or group of healthcare providers) that submitted the healthcare claim transaction may be accessed. In certain embodiments, the product exclusion list may include product information applicable to all prescribers. In other embodiments, the product exclusion list may include respective product information for one or more specified prescribers. Identification information for the identified product may be compared to information included in the product exclusion list, and a determination may be made as to whether a correspondence exists. If it is determined at block 522 that the identified product is a product included in the product exclusion list, then operations may continue at block 506, and the healthcare claim transaction may be marked as suitable for routing to an appropriate claims processor. If, however, it is determined at block 522 that the identified product is not a product included in the product exclusion list, then operations may continue at block 524.

At block 524, a threshold associated with taking a control action and/or with generating an exception for the healthcare claim transaction may be identified. For example, one or more thresholds established by a healthcare provider (or group of healthcare providers) may be identified. A wide variety of different types of thresholds may be utilized as desired in various embodiments of the invention. One example threshold may establish a predetermined number of times that a directions for use exception may be identified or triggered within a given time period (e.g., an hour, a day, a week, a month, etc.). Another example threshold may establish a predetermined number of times that a particular control action may be implemented within a given time period. As desired, a plurality of thresholds may be identified.

At block 526, a determination may be made as to whether one or more identified thresholds have been satisfied. For example, a determination may be made as to whether a threshold number of generated exceptions and/or implemented control actions has been reached. If it is determined at block 526 that an identified threshold has been satisfied, then operations may continue at block 528. At block 528, an indication of a potential at-risk transaction may be stored. For example, information associated with the healthcare claim transaction may be stored in a data repository for potential at-risk transactions. The healthcare claim transaction may then be marked as appropriate for routing to a claims processor. Operations may then end following block 528.

If, however, it is determined at block 526 that an identified threshold has not been satisfied, then operations may continue at block 530. At block 530, a directions for use exception may be identified and/or generated for the healthcare claim transaction.

At block 532, one or more parameters, rules, and/or preferences associated with processing the exception may be identified. For example, one or more exception processing parameters associated with the healthcare provider that submitted the healthcare claim transaction may be identified. In certain embodiments, the parameters may specify desired operations for processing a healthcare claim transaction following the identification of an exception, such as parameters that specify one or more desired control actions.

At block 534, an appropriate control action to be implemented based upon the identified exception may be determined. For example, a control action may be determined based upon an analysis of the identified processing parameters. As desired, different control actions may be taken based upon a wide variety of factors, such as an identification of the healthcare provider, an identification of the prescriber, an identification of the product, an identification of the payer, and/or a number of times that certain control actions have been implemented. Additionally, a wide variety of suitable control actions may be utilized in association with various embodiments of the invention. Examples of suitable control actions include, but are not limited to, generating a rejection for the healthcare claim transaction, adding an identifier to the healthcare claim transaction associated with the exception, and/or storing an indication of the identified exception while still allowing the healthcare claim transaction to be routed to a claims processor.

At block 536, a determination may be made as to whether the determined or identified control action is a rejection action. In other words, a determination may be made as to whether a rejection will be generated based at least in part upon the identified directions for use exception. If it is determined at block 536 that the control action is a rejection action, then operations may continue at block 538. At block 538, a rejection for the healthcare claim transaction may be generated, and the generated rejection may be output for communication to the healthcare provider computer that submitted the healthcare claim transaction. As desired, a wide variety of information may be included in a generated rejection, such as an indication that the healthcare claim transaction has been rejected due to a risk of the prescriber failing to provide appropriate directions for use, an instruction to verify whether appropriate directions for use have been provided, an invitation to resubmit the healthcare claim transaction following verification, and/or override information that may be included in a resubmission to suppress the operations of the directions for use module 180.

If, however, it is determined at block 536 that the control action is not a rejection action, then operations may continue at block 540. At block 540, an indication that the healthcare claim transaction is associated with an at-risk prescriber may be generated. As desired, the indication may be stored in one or more suitable databases or data repositories for subsequent reporting purposes. Additionally, at block 542, the generated indication may be communicated to any number of desired entities, such as the healthcare provider computer or a healthcare provider back office computer. The healthcare claim transaction may then be marked at block 544 as appropriate for routing to a suitable claims processor for adjudication. As an alternative to communicating a separate indication, an indication may be appended to a subsequently received adjudicated reply for the healthcare claim transaction.

The method 500 may end following either block 506, 528, 538, or 544.

The operations described and shown in the methods 300, 400, 500 of FIGS. 3-5 may be carried out or performed in any suitable order as desired in various embodiments of the invention. Additionally, in certain embodiments, at least a portion of the operations may be carried out in parallel. Furthermore, in certain embodiments, less than or more than the operations described in FIGS. 3-5 may be performed.

For example, with reference to FIG. 5, a payer or claims processor for a healthcare claim transaction may also be identified and evaluated when determining whether to trigger a directions for use exception. As one example, payer identification information included in the healthcare claim transaction (e.g., a Banking Identification Number, a Processor Control Number, etc.) may be utilized to identify a payer for the healthcare claim transaction. A determination may then be made as to whether the identified payer is a payer having an associated risk of auditing healthcare claim transactions and/or requesting charge-backs for failure to include appropriate directions for use information. For example, the identification information for the payer may be compared to payer identification information identified from evaluating audit results for previously adjudicated healthcare claim transactions. As another example, the identification information for the payer may be compared to one or more payer inclusion and/or exclusion lists. Based at least in part upon the evaluation of payer information, a determination may be made as to whether to trigger a directions for use exception. In this regard, exceptions may be triggered for payers having a higher risk of auditing the healthcare claim transaction and/or requesting a charge-back.

Accordingly, example embodiments of the invention can provide the technical effects of evaluating healthcare claim transactions in order to determine whether the underlying healthcare transactions and/or prescriptions have a risk of failing to include appropriate directions for use information. The healthcare claim transactions may be evaluated as they are being routed between healthcare providers and payers or claims processors. As a result of the evaluation, economic losses by healthcare providers resulting from subsequent audits on the healthcare claim transactions may be reduced.

Various block and/or flow diagrams of systems, methods, apparatus, and/or computer program products according to example embodiments of the invention are described above. It will be understood that one or more blocks of the block diagrams and flow diagrams, and combinations of blocks in the block diagrams and flow diagrams, respectively, can be implemented by computer-executable program instructions. Likewise, some blocks of the block diagrams and flow diagrams may not necessarily need to be performed in the order presented, or may not necessarily need to be performed at all, according to some embodiments of the invention.

These computer-executable program instructions may be loaded onto a special purpose computer or other particular machine, a processor, or other programmable data processing apparatus to produce a particular machine, such that the instructions that execute on the computer, processor, or other programmable data processing apparatus create means for implementing one or more functions specified in the flow diagram block or blocks. These computer program instructions may also be stored in a computer-readable memory that can direct a computer or other programmable data processing apparatus to function in a particular manner, such that the instructions stored in the computer-readable memory produce an article of manufacture including instruction means that implement one or more functions specified in the flow diagram block or blocks. As an example, embodiments of the invention may provide for a computer program product, comprising a computer usable medium having a computer-readable program code or program instructions embodied therein, said computer-readable program code adapted to be executed to implement one or more functions specified in the flow diagram block or blocks. The computer program instructions may also be loaded onto a computer or other programmable data processing apparatus to cause a series of operational elements or steps to be performed on the computer or other programmable apparatus to produce a computer-implemented process such that the instructions that execute on the computer or other programmable apparatus provide elements or steps for implementing the functions specified in the flow diagram block or blocks.

Accordingly, blocks of the block diagrams and flow diagrams support combinations of means for performing the specified functions, combinations of elements or steps for performing the specified functions and program instruction means for performing the specified functions. It will also be understood that each block of the block diagrams and flow diagrams, and combinations of blocks in the block diagrams and flow diagrams, can be implemented by special purpose, hardware-based computer systems that perform the specified functions, elements or steps, or combinations of special purpose hardware and computer instructions.

Many modifications and other embodiments of the invention set forth herein will be apparent having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A computer-implemented method, comprising:
   receiving, from a healthcare provider computer associated with a healthcare provider, a healthcare claim transaction;
   determining, based upon an analysis of the received healthcare claim transaction, identification information for a prescriber associated with the healthcare claim transaction;
   determining that the identified prescriber is an at-risk prescriber that has previously failed to include appropriate directions for use in association with a prescription;
   evaluating one or more threshold parameters corresponding to a predetermined control action implemented on behalf of the identified at-risk prescriber;
   determining that the one or more threshold parameters corresponding to the predetermined control action have not been satisfied; and
   implementing, based at least upon the determination that the one or more threshold parameters have not been satisfied, the predetermined control action,
   wherein the above operations are performed by one or more computers associated with a service provider.

2. The computer-implemented method of claim 1, wherein determining that the prescriber is an at-risk prescriber comprises:
   accessing stored at-risk information associated with one or more prescribers that have previously failed to include appropriate directions for use in association with prescriptions;
   comparing the prescriber identification information to at least a portion of the accessed at-risk information; and
   determining that the prescriber is an at-risk prescriber based at least in part upon the comparison.

3. The computer-implemented method of claim 2, wherein accessing stored at-risk information comprises accessing information associated with the results of one or more audits that have been performed on previously adjudicated healthcare claim transactions.

4. The computer-implemented method of claim 2, further comprising:
   identifying information associated with one or more products previously prescribed by the at-risk prescriber;

identifying, based upon an analysis of the received healthcare claim transaction, a product associated with the healthcare claim transaction; and determining whether the product associated with the healthcare claim transaction is one of the one or more products previously prescribed by the at-risk prescriber.

5. The computer-implemented method of claim 1, further comprising:

identifying, based upon an analysis of the received healthcare claim transaction, a product associated with the healthcare claim transaction; and determining whether the product is included in one of (i) a product inclusion list or (ii) a product exclusion list associated with the healthcare provider.

6. The computer-implemented method of claim 1, wherein determining that the identified prescriber is an at-risk prescriber comprises determining whether the prescriber is included in one of (i) a prescriber inclusion list or (ii) a prescriber exclusion list associated with the healthcare provider.

7. The computer-implemented method of claim 1, further comprising:

determining whether the healthcare claim transaction is associated with a refill of a prescribed product.

8. The computer-implemented method of claim 1, wherein implementing a predetermined control action comprises:

generating a rejection for the healthcare claim transaction; and communicating the generated rejection to the healthcare provider computer.

9. The computer-implemented method of claim 1, wherein implementing a predetermined control action comprises:

generating an indication that the prescriber associated with the healthcare claim transaction is an at-risk prescriber; and communicating the healthcare claim transaction to a claims processor computer associated with a claims processor.

10. A system, comprising:

at least one memory operable to store computer-executable instructions; and at least one processor configured to access the at least one memory and execute the computer-executable instructions to:

receive, from a healthcare provider computer associated with a healthcare provider, a healthcare claim transaction;

determine, based upon an analysis of the received healthcare claim transaction, identification information for a prescriber associated with the healthcare claim transaction;

determine that the identified prescriber is an at-risk prescriber that has previously failed to include appropriate directions for use in association with a prescription;

evaluate one or more threshold parameters corresponding to a predetermined control action implemented on behalf of the identified at-risk prescriber;

determine that the one or more threshold parameters corresponding to the predetermined control action have not been satisfied; and implement, based at least upon the determination that the one or more threshold parameters have not been satisfied, a predetermined control action.

11. The system of claim 10, wherein the at least one processor is configured to determine that the prescriber is an at-risk prescriber by executing the computer-executable instructions to:

access stored at-risk information associated with one or more prescribers that have previously failed to include appropriate directions for use in association with prescriptions;

compare the prescriber identification information to at least a portion of the accessed at-risk information; and determine that the prescriber is an at-risk prescriber based at least in part upon the comparison.

12. The system of claim 11, wherein the accessed at-risk information comprises information associated with the results of one or more audits that have been performed on previously adjudicated healthcare claim transactions.

13. The system of claim 11, wherein the at least one processor is further configured to execute the computer-executable instructions to:

identify information associated with one or more products previously prescribed by the at-risk prescribers;

identify, based upon an analysis of the received healthcare claim transaction, a product associated with the healthcare claim transaction; and determine whether the product associated with the healthcare claim transaction is one of the one or more products previously prescribed by the at-risk prescribers.

14. The system of claim 10, wherein the at least one processor is further configured to execute the computer-executable instructions to:

identify, based upon an analysis of the received healthcare claim transaction, a product associated with the healthcare claim transaction; and determine whether the product is included in one of (i) a product inclusion list or (ii) a product exclusion list associated with the healthcare provider.

15. The system of claim 10, wherein the at least one processor is configured to perform a risk assessment to determine whether the prescriber is an at-risk prescriber by executing the computer-executable instructions to determine whether the prescriber is included in one of (i) a prescriber inclusion list or (ii) a prescriber exclusion list associated with the healthcare provider.

16. The system of claim 10, wherein the at least one processor is further configured to execute the computer-executable instructions to:

determine whether the healthcare claim transaction is associated with a refill of a prescribed product.

17. The system of claim 10, wherein the at least one processor is configured to implement the predetermined control action by executing the computer-executable instructions to:

generate a rejection for the healthcare claim transaction; and direct communication of the generated rejection to the healthcare provider computer.

18. The system of claim 10, wherein the at least one processor is configured to implement the predetermined control action by executing the computer-executable instructions to:

generate an indication that the prescriber associated with the healthcare claim transaction is an at-risk prescriber; and direct communication of the healthcare claim transaction to a claims processor computer associated with a claims processor.

* * * * *